United States Patent
Lackmann et al.

(10) Patent No.: US 7,960,513 B2
(45) Date of Patent: Jun. 14, 2011

(54) ANTIBODY AGAINST A HUMAN ADAM PROTEASE

(75) Inventors: Martin Lackmann, Clayton (AU); Peter W. Janes, Clayton (AU); Dimitar B. Nikolov, New York, NY (US); Nayanendu Saha, Calcutta (IN)

(73) Assignees: Monash University, Clayton, Victoria (AU); Memorial Sloan Kettering Cancer Center, New York, NY (US)

( * ) Notice: Subject to any disclaimer, the term of this patent is extended or adjusted under 35 U.S.C. 154(b) by 374 days.

(21) Appl. No.: 11/721,949

(22) PCT Filed: Dec. 19, 2005

(86) PCT No.: PCT/AU2005/001917
§ 371 (c)(1),
(2), (4) Date: Aug. 1, 2008

(87) PCT Pub. No.: WO2006/063415
PCT Pub. Date: Jun. 22, 2006

(65) Prior Publication Data
US 2008/0317763 A1    Dec. 25, 2008

Related U.S. Application Data

(60) Provisional application No. 60/637,425, filed on Dec. 17, 2004.

(51) Int. Cl.
*C07K 16/40* (2006.01)
(52) U.S. Cl. .......... 530/387.1; 530/350; 530/388.1; 530/388.26
(58) Field of Classification Search .......... None
See application file for complete search history.

(56) References Cited

OTHER PUBLICATIONS

Zou et al, Catalytic activity of human ADAM33. J Biol Chem. Mar. 12, 2004;279(11):9818-30. Epub Dec. 15, 2003.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Ngo et al. Computational complexity, protein structure prediction, and the Levinthal paradox. The Protein Folding Problem and Tertiary Structure Prediction, pp. 492-495, 1994.*
Lederman et al. A single amino acid substitution in a common African allele of the CD4 molecule ablates binding of the monoclonal antibody, OKT4. Mol Immunol. 28(11):1171-1181, 1991.*
Li et al. beta-Endorphin omission analogs: dissociation of immunoreactivity from other biological activities.Proc Natl Acad Sci U S A. 77(6):3211-3214, 1980.*
Rosendahl et al. Identification and characterization of a pro-tumor necrosis factor-alpha-processing enzyme from the ADAM family of zinc metalloproteases. J Biol Chem 272(39): 24588-24593, 1997.*
Daniel et al. Virology 202: 540-549, 1994.*
R&D Systems technical datasheet for Mab1427; internet release Jun. 2, 2003 and print release Jun. 1, 2003; 2 pages.*
R&D Systems technical datasheet for Ab936; internet release Apr. 14, 2003 and Jun. 1, 2003; 2 pages.*
R&D Systems 2004 Catalog listing for Mab1427 and Ab936; title page and p. 323.*
Frayne et al., *Molecular Human Reproduction*, 8(9): 817-822 (2002).
Huang et al., *Development*, 130(14): 3147-3161 (2003).
Janes et al., *Cell*, 123(2): 291-304 (Oct. 21, 2005).
Loechel et al., *FEBS Letters*, 506: 65-68 (Sep. 2001).
Reddy et al., *Journal of Biological Chemistry*, 275(19): 14608-14614 (May 12, 2000).
Smith et al., *Journal of Cell Biology*, 159(5): 893-902 (Dec. 9, 2002).

* cited by examiner

*Primary Examiner* — Bridget E Bunner
(74) *Attorney, Agent, or Firm* — Leydig, Voit & Mayer, Ltd.

(57) ABSTRACT

Elucidation of the crystal structure of an ADAM10 substrate-recognition and proteinase-positioning module comprising the protein cysteine-rich and disintegrin domains, and detailed functional analysis revealed that an acidic pocket within the cysteine-rich domain forms a substrate-recognition site. The binding of this pocket to receptor/ligand complexes facilitates effective ligand cleavage, which is prevented when critical residues within the pocket are changed. This provides use of the surface pocket within the extracellular domain of ADAM10, and the corresponding structure in related proteases such as ADAM17, as a target for structure-based computational and high-throughput screens for small-molecule substrate-specific inhibitors or monoclonal antibodies that inhibit ADAM protease cleavage of ephrins and other ADAM10 or ADAM17 substrates. These inhibitors will be useful in therapeutic intervention of tumour development, invasion and metastasis and other diseases which involve the activity of the ADAM10 and ADAM17 proteases, such as inflammation, cardio-vascular disease, arthritis and other auto-immune diseases.

3 Claims, 6 Drawing Sheets

Figure 3A

ANTIBODY AGAINST A HUMAN ADAM PROTEASE

CROSS-REFERENCE TO RELATED APPLICATIONS

This patent application is the U.S. national phase of International Patent Application No. PCT/AU2005/001917, filed on Dec. 19, 2005, which claims the benefit of U.S. Provisional Patent Application No. 60/637,425, filed Dec. 17, 2004.

INCORPORATION-BY-REFERENCE OF MATERIAL SUBMITTED ELECTRONICALLY

Incorporated by reference in its entirety herein is a computer-readable nucleotide/amino acid sequence listing identified as follows: One 15,119 Byte ASCII (Text) file named "701671.TXT," created on Aug. 1, 2008.

FIELD OF THE INVENTION

THIS INVENTION relates to a metalloprotease that mediates proteolytic cleavage of proteins located at the cell surface. More particularly, this invention relates to ADAM 10 and/or ADAM17 metalloprotease-mediated proteolytic cleavage of substrate proteins, such as ligands for Eph and epidermal growth factor (erbB) receptors, and elucidation of the ADAM metalloprotease domains and amino acid residues that are critical for recognition of, and interaction with, such proteins. The invention also relates to the design and discovery of molecules that modulate ADAM10- and/or ADAM 17-mediated proteolytic cleavage of substrate proteins.

BACKGROUND OF THE INVENTION

ADAM (A Disintegrin And Metalloprotease) metalloproteases cleave extracellular domains of membrane-tethered proteins in a regulated, substrate-specific manner, yet without apparent preference for a cleavage sequence signature. Among other substrates, ADAM10 and ADAM17 cleave ligands for several receptor tyrosine kinase ligands, including EGF, HB-EGF, TGF-α, amphiregulin, betacellulin, epiregulin), the TNF-receptor ligand TNF-α and ephrins (Steals & Courtneidge, 2003, Genes & Dev. 17 7-30). Ephrin cleavage by ADAM10 enables cell-contact repulsion between Eph and ephrin expressing cells to proceed (Hattori et al., 2000, Science 289 1360), but how this is regulated has remained unclear.

Eph receptors and their membrane-bound ephrin ligands mediate cell positioning and pathfinding during development. Ephrin-Eph interactions on opposing cells lead to bi-directional signalling and typically induce cell-cell repulsion. Upon cell-cell contact, the interacting Ephs and ephrins form heterotetramers, which are further assembled in large signalling clusters (Himanen & Nikolov, 2003, Trends Neurosci. 26 46-51; Wimmer-Kleikamp et al., 2004, J. Cell Biol. 164 661-666).

This creates multivalent molecular tethers between opposing cell surfaces of the interacting cells that must necessarily be overcome to enable cell repulsion and signal termination.

To date two general mechanisms have been proposed that allow termination of Eph/ephrin-mediated cell contacts. EphB4-ephrinB2 interaction is thought to induce trans-endocytosis of the entire ephrin-Eph complex into either cell, in a manner dependent on the intracellular domains of both ephrin and Eph (Zimmer et al., 2003, Nat. Cell Biol. 5 869-78), and on Rac signalling (Marston et al., 2003, Nat. Cell Biol, 5 879-88).

An alternative mechanism involves ephrin cleavage by transmembrane proteases, first observed for the GPI (glycosylphosphatidylinositol)-anchored ephrin-A2, which is cleaved by the metalloprotease ADAM10. As this cleavage is essential for disrupting the Eph/ephrin cell tether, expression of an uncleavable ephrin-A2 mutant inhibits axon repulsion in neuronal cells (Hattori et al., 2000, supra). Ephrin-A2 cleavage was found to be enhanced by the presence of the EphA3 extracellular domain, and a conserved region within the Eph-binding domain of ephrins (Himanen et al., 1998, Nature 396 486-91), that appeared to promote cleavage by ADAM10, was suggested as a candidate interaction interface. The subsequently determined structures of two Eph/ephrin complexes (Himanen et al., 1998, supra; Himanen, et al., 2004, Nat. Neurosci. 7 501-509) revealed, however, that this ephrin region is involved in receptor binding and would be unavailable for ADAM interactions upon formation of an Eph/ephrin complex.

It therefore still remained unclear how ADAM proteases interact with ephrins, and how this might be regulated to ensure cleavage of only Eph-bound ephrin molecules.

SUMMARY OF THE INVENTION

The present invention is broadly directed to the identification, isolation and use of domain(s) and/or amino acid residues of an ADAM protease that mediate interaction with substrate proteins, including, but not limited to substrates such as ligands for Eph and epidermal growth factor receptors, and protein complexes comprising said ligands and receptors.

In one particular broad form, the invention is directed to use of a cysteine-rich domain of an ADAM protease and/or amino acid residues within said cysteine-rich domain that mediate interaction with a substrate protein, to identify, design or otherwise produce a modulator of ADAM recognition, binding and/or proteolytic cleavage of a substrate protein.

In a preferred form, the ADAM protease is ADAM10 or ADAM17.

In a first aspect, the invention provides an ADAM protease, or fragment thereof, having a modified ability to recognise, bind and/or proteolytically cleave a substrate protein compared to a wild-type ADAM protease.

Preferably, the modified ADAM protease, or fragment thereof, is incapable of recognizing, binding and/or proteolytically cleaving said substrate protein, or has a reduced ability compared to said wild-type ADAM protease.

In a preferred embodiment, the modified ADAM protease or fragment thereof comprises one or more non-conservative amino acid substitutions in an extracellular domain of said ADAM protease.

Preferably, the one or more amino acid substitutions are in the cysteine-rich domain of the ADAM protease extracellular domain.

In particular embodiments relating to ADAM10 protease, the one or more amino acid substitutions are selected from the group consisting of a Glu573 substitution, a Glu578 substitution and a Glu579 substitution.

In particular embodiments relating to ADAM17 protease, the one or more amino acid substitutions are selected from the group consisting of a Glu583 substitution, a Glu589 substitution and a Ser590 substitution.

Preferably, in embodiments relating to ADAM10, the substrate protein is an A-type ephrin present in a protein complex further comprising an A-type Eph receptor.

Preferably, in further embodiments relating to ADAM10, the substrate protein is an EGF-type ligand precursor protein present in a protein complex further comprising an EGF receptor.

In one particular embodiment relating to ADAM10, the A-type ephrin is ephrin-A5 or ephrin A2 and the A-type Eph is EphA3.

In another particular embodiment relating to ADAM10, the EGF-type ligand precursor is pro-EGF or pro-betacellulin.

In one particular embodiment relating to ADAM17, the ephrin is ephrin B2 and the Eph is EphB2 or EphB4.

In another particular embodiment relating to ADAM17, the EGF-type ligand precursor is pro-Hb-EGF, pro-amphiregulin or TGF-α.

In a second aspect, the invention provides an isolated protein complex comprising an ADAM protease fragment or the modified ADAM protease of the first aspect, and a substrate protein.

Preferably, the ADAM protease fragment is a cysteine-rich region of ADAM protease extracellular domain.

In one embodiment, the ADAM protease fragment comprises residues Phe552-Arg646 of human ADAM10 protease.

In another embodiment, the ADAM protease fragment comprises residues Asp564-Arg644 of human ADAM17 protease.

In one particular embodiment relating to ADAM10, the substrate protein is ephrin-A5, ephrin-A2, pro-EGF and/or pro-betacellulin.

Preferably, ephrin-A5 or ephrin-A2 are present in an isolated protein complex further comprising EphA3.

Preferably, pro-EGF or pro-betacellulin are present in a complex further comprising EGF-receptor erbB1.

In one particular embodiment relating to ADAM17, the substrate protein is ephrin-B2, pro-Hb-EGF, pro-amphiregulin or pro-TGFα.

Preferably, ephrin-B2 is present in an isolated protein complex comprising EphB2 or EphB4.

Preferably, pro-Hb-EGF, pro-amphiregulin or pro-TGF-α are in an isolated protein complex comprising the EGF-receptor erbB1.

In a third aspect, the invention provides an isolated nucleic acid encoding the modified ADAM protease, or fragment thereof, of the first aspect.

In a fourth aspect, the invention provides a genetic construct comprising the isolated nucleic acid of the third aspect.

In a fifth aspect, the invention provides a host cell comprising the genetic construct of the fourth aspect.

In a sixth aspect, the invention provides an antibody raised against or capable of binding a substrate recognition site within a cysteine-rich domain of an ADAM protease.

Preferably, the antibody is capable of binding the substrate recognition site of the ADAM protease, to thereby reduce affinity for the substrate and prevent substrate cleavage.

Suitably, the substrate recognition site is in a cysteine-rich domain of an ADAM protease comprising residues Phe552-Arg 646 of human ADAM10 protease or a cysteine-rich region comprising residues Asp564-Arg644 of ADAM17 protease.

In another embodiment, the antibody is raised against or capable of binding the modified ADAM protease or fragment thereof of the first aspect.

Suitably, the antibody binds a wild-type ADAM protease or fragment thereof with relatively reduced affinity compared to said modified ADAM protease or fragment thereof.

In a seventh aspect, the invention provides a method of producing a modified ADAM protease, or fragment thereof, that has a modified ability to recognize, bind and/or proteolytically cleave a substrate protein, compared to a wild-type ADAM protease, said method including the steps of:

(i) introducing one or more amino acid substitutions into an ADAM protease or fragment thereof, or into a nucleic acid encoding same, to thereby produce a modified ADAM protease or fragment thereof; and (ii) determining whether said modified ADAM protease, or fragment thereof, proteolytically cleaves and/or binds a substrate protein, or has a modified ability compared to a wild-type ADAM protease.

Preferably, the modified ADAM protease, or fragment thereof is incapable of recognizing, binding and/or proteolytically cleaving said substrate protein, or has a reduced ability compared to a wild-type ADAM protease.

In one embodiment, the ADAM protease fragment comprises residues Phe 552-Arg 646 of human ADAM10 protease.

In another embodiment, the ADAM protease fragment comprises residues Asp564-Arg644 of ADAM17 protease.

In an eighth aspect, the invention provides a method of producing a modulator of an ADAM protease including the step of using the modified ADAM protease or fragment thereof of the first aspect, or a protein construct comprising a cysteine-rich domain of an ADAM protease, to identify, design, screen or otherwise produce a modulator of an ADAM protease.

In one form, this aspect provides a method of producing a modulator of an ADAM protease including the step of using the modified ADAM protease or fragment thereof of the first aspect, to identify, design, screen or otherwise produce a modulator of an ADAM protease.

In another form, this aspect provides a method of producing a modulator of an ADAM protease including the step of using a cysteine rich domain of an ADAM protease, or one or more amino acid residues thereof, to identify, design, screen or otherwise produce a modulator of an ADAM protease.

Preferably, the amino acid residues of ADAM10 are selected from the group consisting of: Glu573, Glu578 and Glu579.

Preferably, the amino acid residues of ADAM17 are selected from the group consisting of: Glu583, Glu589 and Ser590.

In a particular embodiment, said modulator is an inhibitor of ADAM10 or ADAM17 protease, which inhibitor is capable of reducing, preventing or blocking substrate recognition, binding and/or proteolytic cleavage of one or more cell surface proteins by said ADAM10 or ADAM17 protease.

In a ninth aspect, the invention provides a pharmaceutical composition comprising a modulator of an ADAM protease and a pharmaceutically-effective carrier, diluent or excipient.

Preferably, said modulator inhibits ADAM protease recognition, binding and/or proteolytic cleavage of one or more cell surface proteins.

In one particular embodiment, the modulator is an inhibitor of ADAM10 cleavage of ephrin-A5, ephrin-A2, pro-EGF and/or pro-betacellulin.

In another particular embodiment, the modulator is an inhibitor of ADAM17 cleavage of ephrin-B2, pro-Hb-EGF, pro-amphiregulin or pro-TGF-α.

One non-limiting example of an inhibitor of ADAM according to this embodiment is a fragment of ADAM10 protease that consists essentially of the cysteine-rich region of the ADAM10 protease extracellular domain.

Another non-limiting example of an inhibitor of ADAM according to this embodiment is a fragment of ADAM17 protease that consists essentially of the cysteine-rich region of the ADAM17 protease extracellular domain.

Yet another non-limiting example of an inhibitor is an antibody according to the sixth aspect or a small molecule inhibitor.

In a tenth aspect, the invention provides a method of a prophylactically or therapeutically treating a disease or condition responsive to modulation of ADAM activity in an animal, said method including the step of administering a modulator of ADAM to said animal to thereby modulate ADAM activity.

Preferably, said modulator inhibits ADAM recognition, binding and/or proteolytic cleavage of one or more cell surface proteins of said animal.

In particular embodiments, the disease or condition responsive to negative modulation of ADAM protease activity is tumour development, tumour invasion and/or metastasis, neurite outgrowth (e.g. potential recovery from spinal injury), inflammatory conditions such as reheumatoid arthritis and cardiac hypertrophy.

In other embodiments, the invention provides treatments of diseases that are responsive to positive modulation of ADAM protease activity, such as Alzheimers disease.

Said animal is preferably a mammal, inclusive of humans, livestock, performance animals, companion animals and the like.

Preferably, said animal is a human.

Throughout this specification, unless otherwise indicated, "comprise", "comprises" and "comprising" are used inclusively rather than exclusively, so that a stated integer or group of integers may include one or more other non-stated integers or groups of integers.

Figure 1:
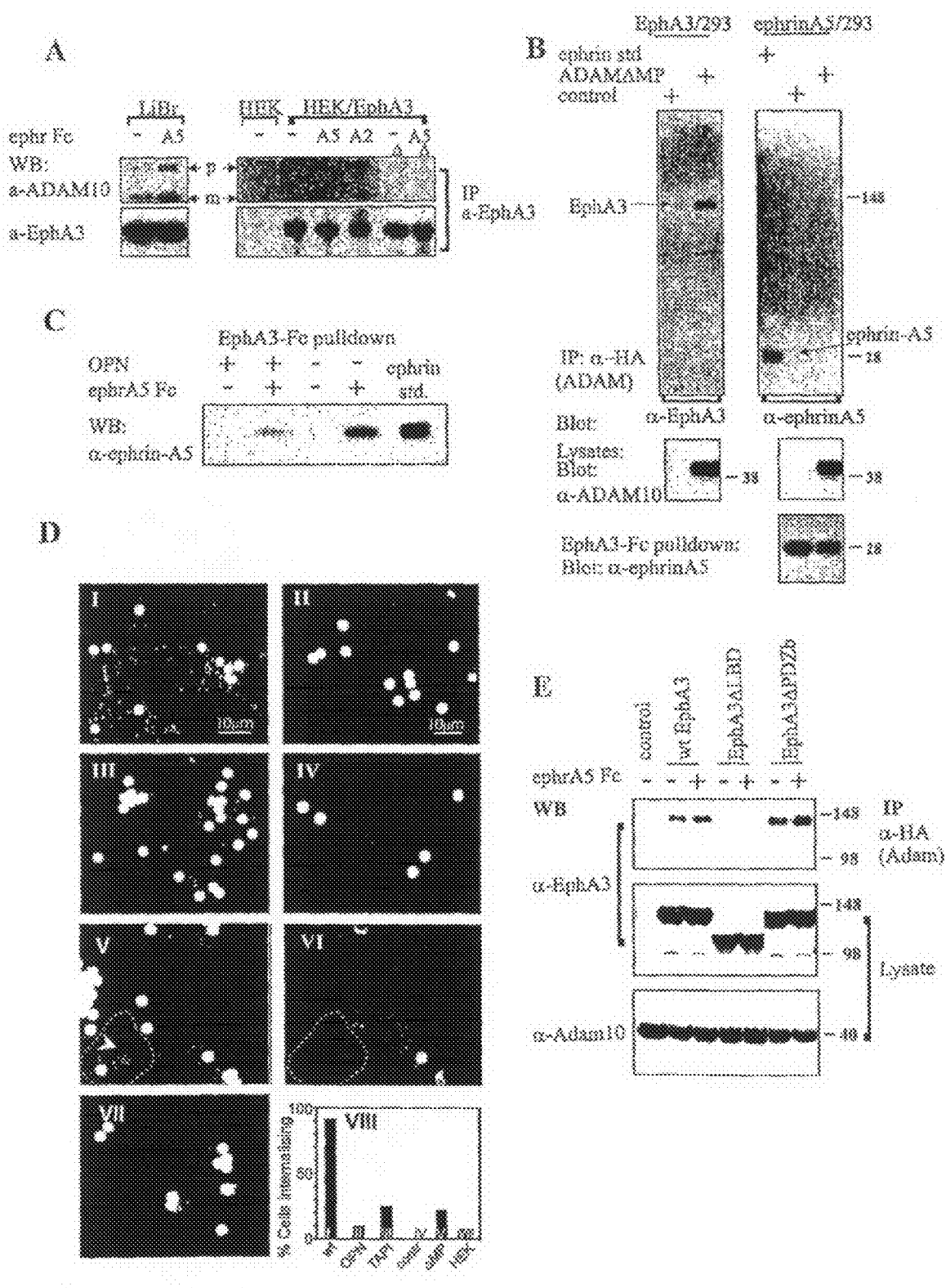
FIG. 1. EphA3-ADAM10 association, ephrin-A5 cleavage and ephrin internalisation.

A. Association of ADAM10 with EphA3 in LiBr melanoma cells and parental or stably transfected EphA3/HEK293 cells. The cells were treated with clustered ephrin-Fc (A5 or A2) or were left untreated (–) prior to lysis. Anti-EphA3 immunoprecipitates from lysates were analysed by Western blot for endogenous ADAM10 ("p" and "m" indicate the pro (unprocessed) and mature (processed) forms of ADAM10). Aliquots from immunoprecipitates were blotted for EphA3 levels to indicate loading (lower panel). Arrowheads "Δ" indicate lanes where the specificity of ADAM10 detection was verified by blocking of anti-ADAM10 antibodies during immunoblot with recombinant ADAM10$_{\Delta MP}$.

B. EphA3, but not ephrin-A5 interacts with dominant-negative ADAM10. EphA3/HEK293 or ephrin-A5/HEK293 cells were transfected to express HA-tagged ADAM10$_{\Delta PM}$. Western Blots of anti-HA immuno-precipitates were analysed with antibodies against ephrin-A5 and EphA3, parallel control samples with anti-ADAM10 antibodies. Lysates of ephrin-A5/HEK 293 cells were also extracted with Protein-A Sepharose-bound EphA3 Fc and analysed with anti-ephrin-A5 antibodies.

C. Ephrin-A5 pre-clustering is required for metalloprotease-mediated cleavage. EphA3/293 cells with (+) or without (–) exposure to 1,10-O-Phenanthroline (OPN) were treated with clustered (+) or non-clustered (–) ephrin-A5-Fc. Pooled cell lysates and supernatants were pre-cleared with excess Protein-A Sepharose, cleaved ephrin-A5 was extracted using EphA3-Fc coupled to Protein-A Sepharose and analysed by anti-ephrin-A5 immuno-blot. Recombinant, monomeric, single-chain ephrin-A5 (Himanen et al., 2004, Nat Neurosci. 7 501-9; ephrin std) was analysed in parallel.

D. Ephrin-A5 cleavage and internalisation are inhibited by dominant-negative ADAM10. EphA3-overexpressing EphA3/293 cells (panels I-VI), or parental BEK293 cells (panel VII) were incubated for 30 min with Alexa$^{546}$-labelled ephrinA5-Fc beads (panels I-III, V-VII) or Alexa-Fc control beads (panel IV), fixed and analysed for internalised ephrin-A5 by confocal microscopy. Cells were pretreated as follows: panels I, IV, VII: no pretreatment; panel II: pretreated with 1 mM OPN; panel III pretreated with 50 μM TAPI1, panel V, VI: transiently transfected with HA-ADAM10$_{\Delta MP}$. The images of the Alexa$^{546}$-fluorescence are shown in panels I-V. The expression of dominant-negative ADAM10$_{\Delta MP}$, assessed using anti-HA (α-HA) and Alex$^{488}$-conjugated secondary antibodies, is illustrated in green. Arrowhead denotes a cell (outlined in panels V, VI) with a dotted line) expressing no detectable ADAM10$_{\Delta MP}$ and containing internalised ephrin-A5. Scale bar: 10 μm, The percentage of cells bound by beads that internalised ephrin-A5 is shown in Panel VIII.

E. The EphA3 ligand-binding domain is required for constitutive and ephrin-induced ADAM binding. HEK293 cells were transfected with HA-ADAM10$_{\Delta MP}$ alone (control) or together with wt EphA3 or EphA3 truncation mutants lacking the N-terminal ligand-binding domain (ΔLBD) or the C-terminal PDZ-binding domain (ΔPDZb). Anti-HA immunoprecipitates and total lysates from cells treated with (+) or without (–) cross-linked ephrin-A5-Fc were analysed by Western blotting with the indicated antibodies.

Figure 2:
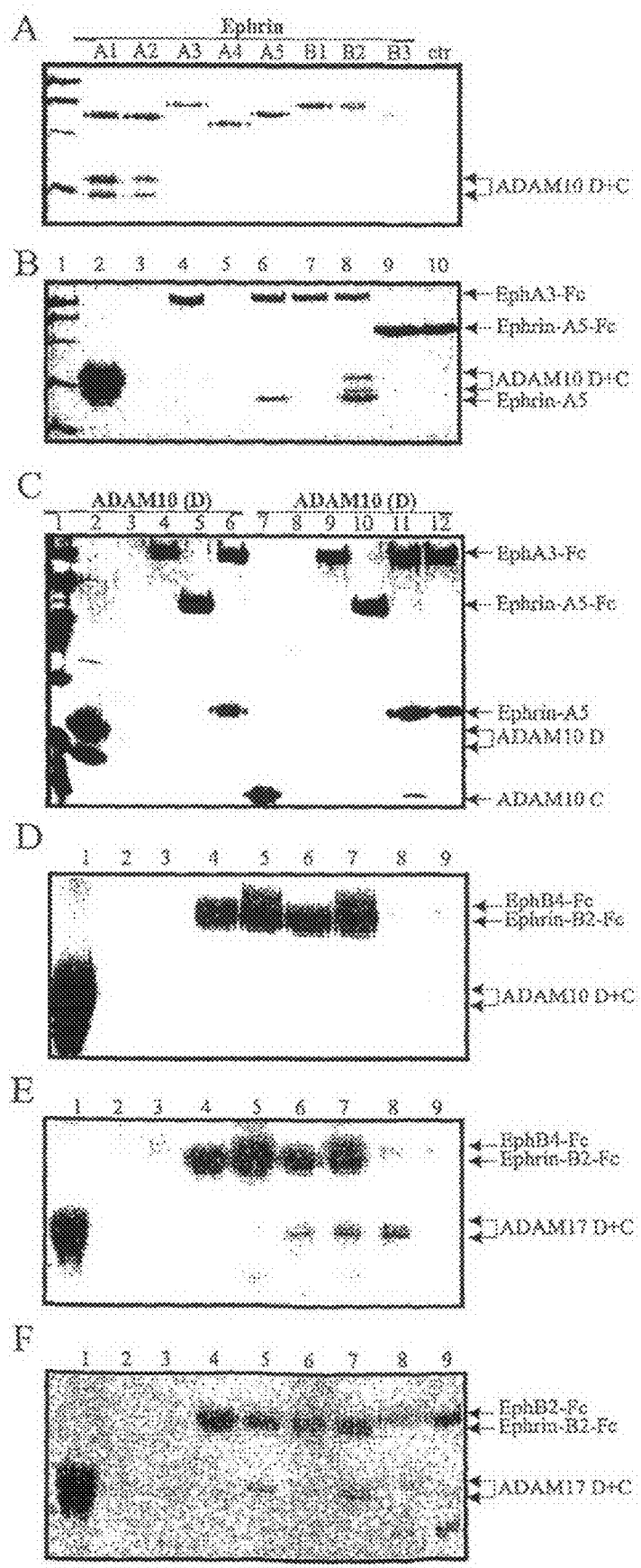

FIG. 2. Interactions of ADAM10 with EphA3, ephrin-A5 and ephrin-A2, and of ADAM17 with EphB2, EphB4 and ephrin-B2.

A. ADAM10 disintegrin and cysteine-rich domain (ADAM10$_{D+C}$) binding to various ephrins in vitro. Fc fusion proteins of the indicated ephrins were co-incubated with ADAM10$_{D+C}$, ephrin-Fc-bound proteins recovered on Protein A Sepharose and analysed by SDS-PAGE and silver staining. The control lane (—) shows Protein A-bound ADAM10$_{D+C}$ incubated alone.

B. The ADAM10$_{D+C}$ domain binds the EphA3/ephrin-A5 complex but not the individual proteins. EphA3-Fc, ephrin-A5 and ADAM10$_{D+C}$ were incubated together in various combinations (below), recovered on Protein A Sepharose and analysed by SDS-PAGE and silver staining. Ephrin-A5-Fc binding to ADAM10$_{D+C}$ was also tested in the absence of EphA3 (lanes 9 and 10). Lane 1: markers. Lane 2: ADAM10$_{D+C}$ input (15 μg). Lanes 3-10: Protein A pull-downs; 3: ADAM10$_{D+C}$; 4: EphA3-Fc; 5: ephrin-A5; 6: EphA3-Fc+ephrin-A5; 7: ADAM10$_{D+C}$+EphA3-Fc; 8: ADAM10$_{D+C}$+EphA3-Fc+ephrin-A5; 9: ephrin-A5-Fc; 10: ADAM10$_{D+C}$+ephrin-A5-Fc.

C. The ADAM10 cysteine-rich domain alone binds the EphA3/ephrin-A5 complex. The ADAM10 disintegrin (1), lanes 2-6) and cysteine-rich (C, lanes 7-11) domains were incubated alone (D, lane 2; C, lane 7) or together with EphA3-Fc and ephrin-A5 (as detailed below), and Protein A-bound proteins were analysed as in panels a), b). Lanes 2, 7: ADAM D and C protein inputs, respectively; lanes 3, 8: ADAM D and C constructs alone, respectively or co-incubated with EphA3-Fc (4, 9); with ephrin-A5-Fc (5 and 10): or with EphA3-Fc and ephrin-A5 (6 and 11). Lane 12; ephrin-A5 incubated with EphA3-Fc.

D. The ADAM10$_{D+C}$ domain does not bind the EphB4/ephrin-B2 complex. EphB4-Fc, ephrin-B2 and ADAM10$_{D+C}$ were incubated together in various combinations and captured on ProteinA beads: lane 1, ADAM10$_{D+C}$ alone; lane 2: ADAM10$_{D+C}$/ProteinA; lane 3, EphB4/ProteinA; lane 4, ephrin-B2 Fc/ProteinA; lane 5, ephrin-B2-Fc, EphB4/ProteinA; lane 6, ephrin-B2-Fc, ADAM10$_{D+C}$/ProteinA; lane 7, ephrin-B2-Fc, EphB4, ADAM11+/ProteinA; lane 8, EphB4-Fc, ADAM10$_{D+C}$/ProteinA; lane 9, EphB4-Fc:

E. The ADAM17$_{D+C}$ domain binds the EphB4/ephrin-B2 complex. Lane 1, ADAM17$_{D+C}$ alone; lane 2: ADAM17$_{D+C}$/ProteinA; lane 3, EphB4/ProteinA; lane 4, ephrin-B2 Fc/ProteinA; lane 5, ephrin-B2-Fc, EphB4/ProteinA; lane 6, ephrin-B2-Fc, ADAM17$_{D+C}$/ProteinA; lane 7, ephrin-B2-Fc, EphB4, ADAM17$_{D+C}$/ProteinA; lane 8, EphB4-Fc, ADAM17$_{D+C}$/ProteinA; lane 9, EphB4-Fc.

F. The ADAM17$_{D+C}$ domain binds the EphB2/ephrin-B2 complex. Lane 1, ADAM17$_{D+C}$ alone; lane 2: ADAM17$_{D+C}$/ProteinA; lane 3, EphB2/ProteinA; lane 4, ephrin-B2 Fc/ProteinA; lane 5, ephrin-B2-Fc, EphB2 (1 µg), ADAM17$_{D+C}$/ProteinA; lane 6, ephrin-B2-Fc, ADAM17$_{D+C}$/ProteinA; lane 7, ephrin-B2-Fc, EphB2 (2 µg), ADAM17$_{D+C}$/ProteinA; lane 8, EphB2-Fc, ADAM17$_{D+C}$/ProteinA; lane 9, EphB2-Fc.

Figure 3A:
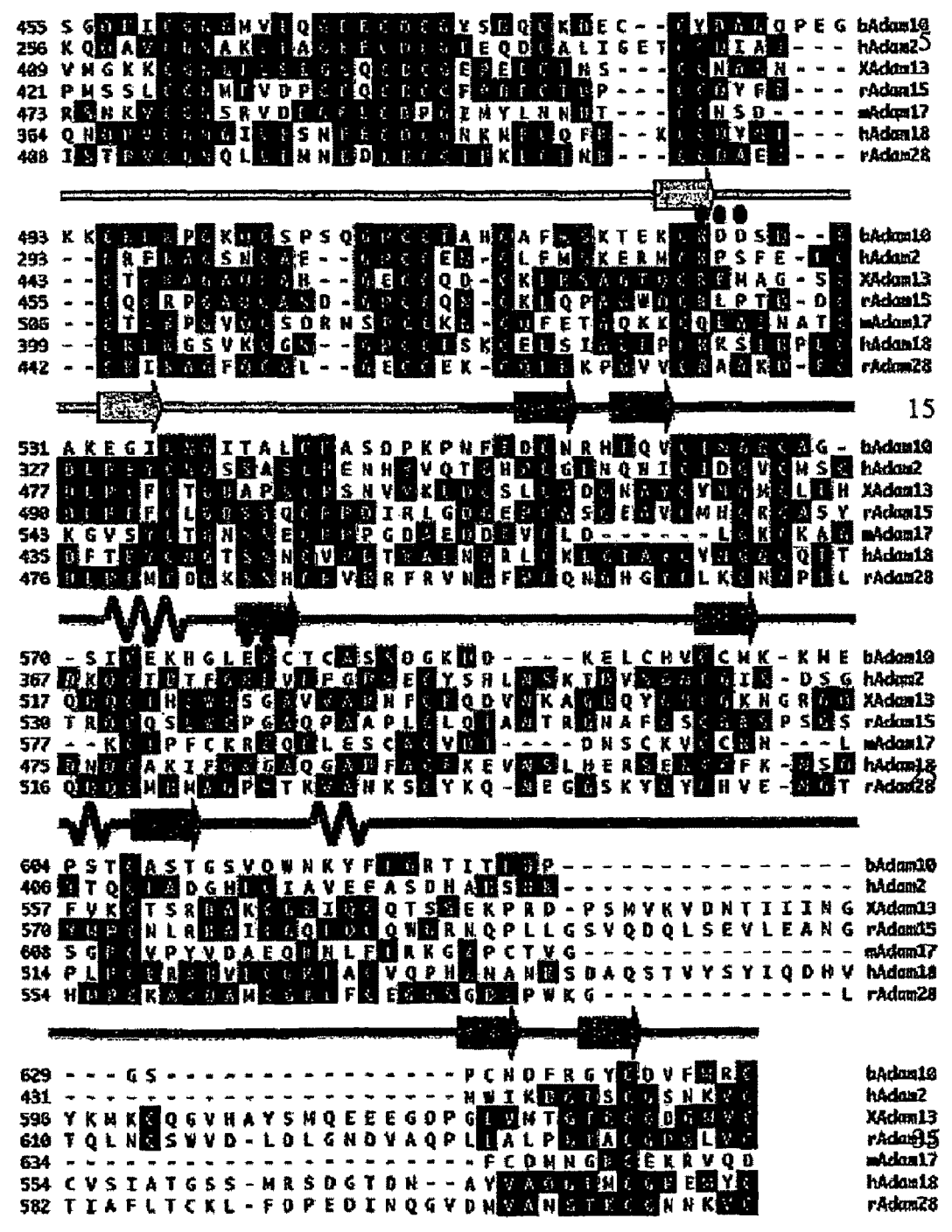
Figure 3:
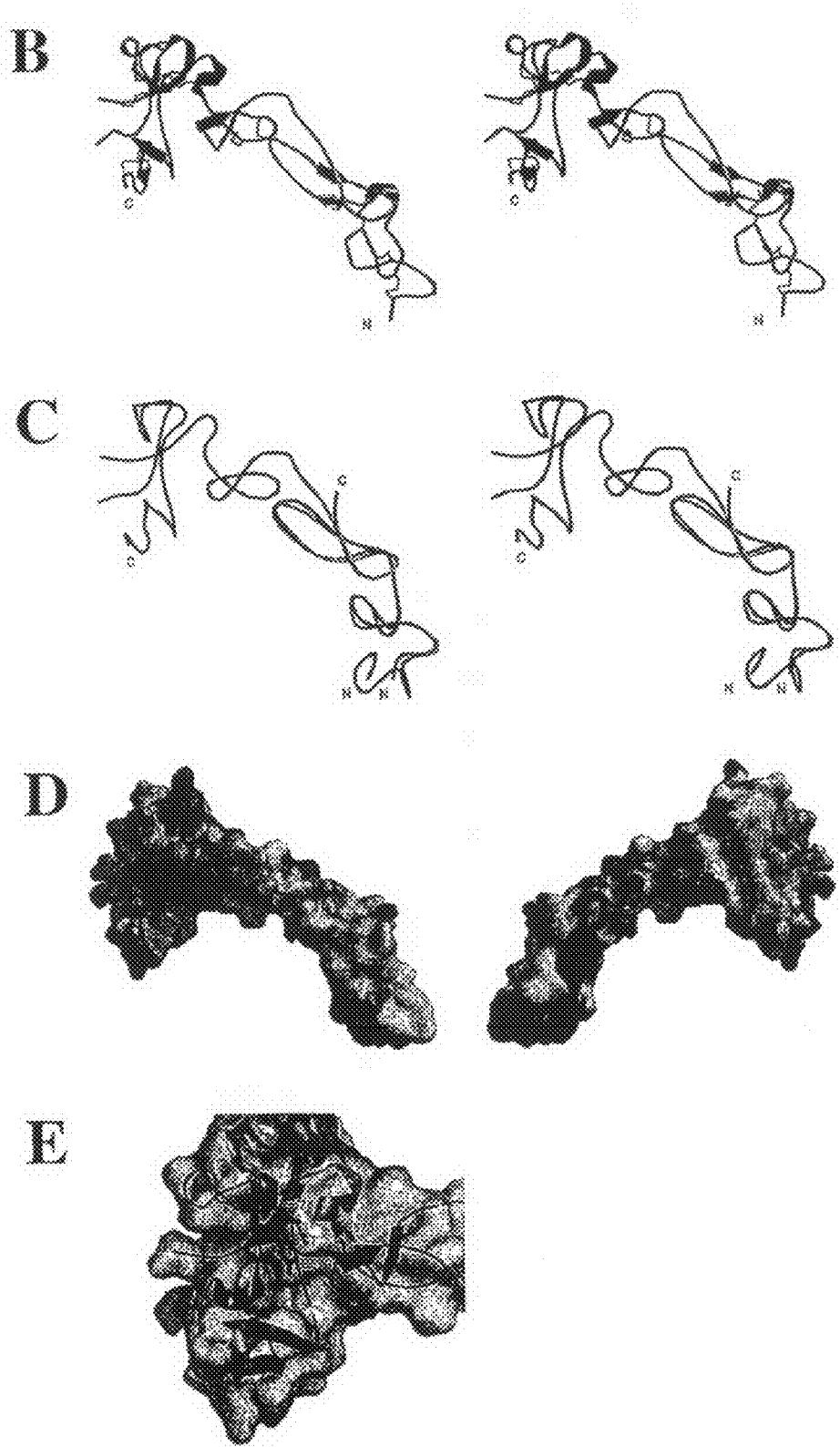

FIG. 3. Structure of the ADAM10 disintegrin and cysteine-rich domains (SEQ ID NOS :14-20).

A. Structure-based alignment of the Disintegrin and Cys-rich region of various ADAMs.

B. Stereoview of the ADAM10$_{D+C}$ structure. The N and C termini are indicated.

C. Stereoview of the ADAM10$_{D+C}$ structure superimposed on the structure of the disintegrin trimestatin (1j2l (21).

D. The molecular surface of ADAM10$_{D+C}$, two 180° –rotated views are shown.

E. Close-up view of the acidic pocket showing the three Glu residues targeted by mutagenesis.

Figure 4:
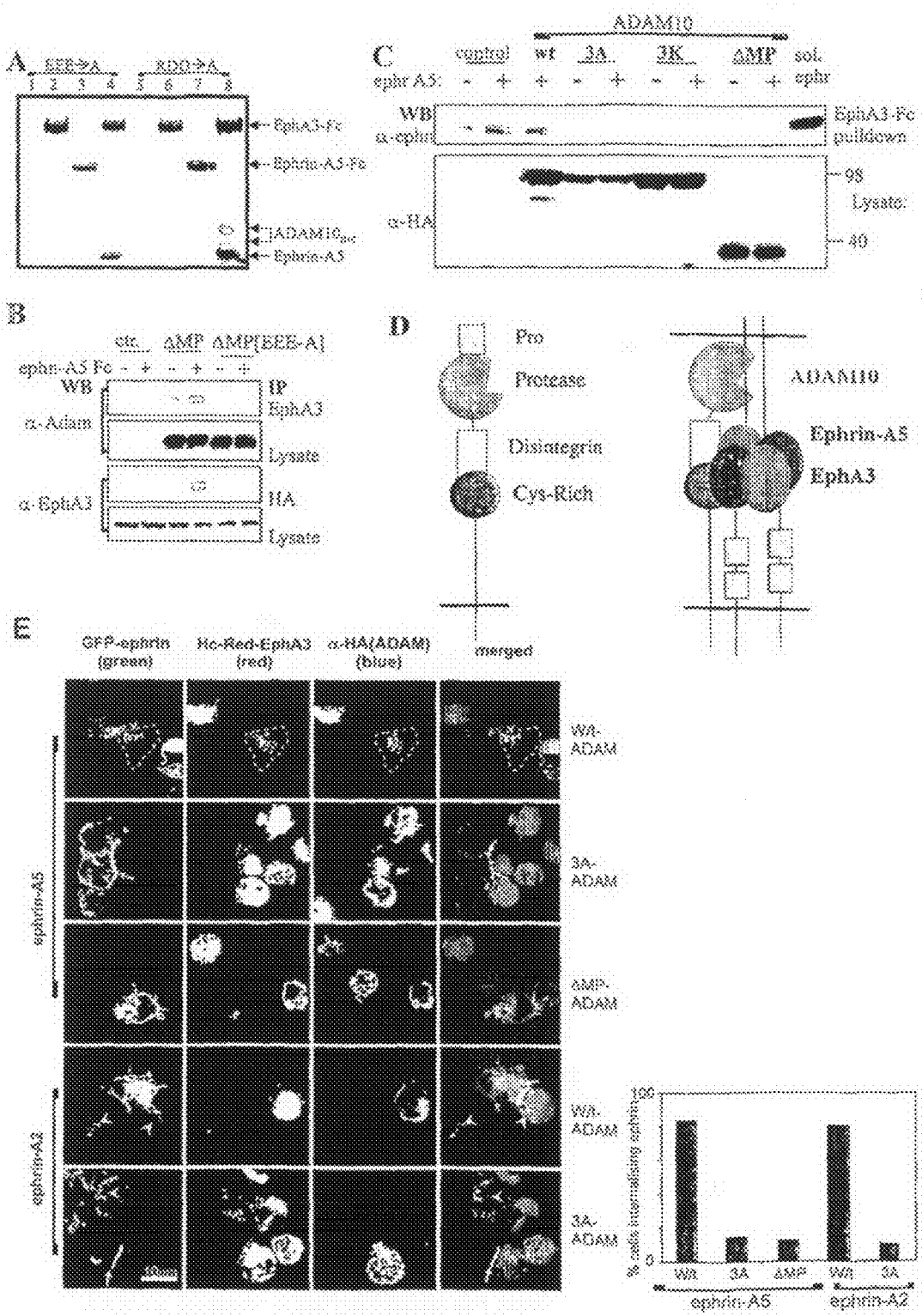

FIG. 4. Mutation of acidic residues in the ADAM10 Cys-rich domain affects binding to EphA3/ephrin-A5 and cleavage of ephrin-A5.

A. In vitro binding of mutant ADAM10$_{D+C}$ to EphA3/ephrin-A5. ADAM10$_{D+C}$[EEE-A] containing Alanine substitutions of Glu$_{573}$, Glu$_{578}$, Glu$_{579}$ (lanes 1-4) or ADAM10$_{D+C}$[RDD-A] (Ala substitutions of Arg$_{525}$, Asp$_{526}$, Asp$_{527}$, lanes 5-8) were incubated alone (lanes 1, 5), or together with EphA3-Fc (lanes 2, 6), ephrin-A5-Fc (lanes 3, 7), or EphA3-Fc and ephrin-A5 (lanes 4, 8). Complexed proteins were extracted with Protein-A-Sepharose beads and analysed as in FIG. 2.

B. Binding of wild-type and mutant ADAM10$_{AMP}$ to EphA3 in cells. EphA3/293 cells were transfected with HA-ADAM10$_{AMP}$ or HA-ADAM10$_{AMP}$ [EEE-A]. Parental and transfected cells were treated for 10 min with or without pre-clustered ephrin-A5-Fc and lysed. Anti-HA and anti-EphA3 immunoprecipitates, and total cell lysates were analysed by Western blotting with indicated antibodies.

C. Ephrin-A5-Fc cleavage in cells expressing wt and 3A mutant ADAM10. EphA3/293 cells were transfected with full length, wild-type (wt) ADAM10, dominant-negative ADAM10$_{AMP}$, or ADAM10 bearing alanine (3A) or 3 lysine (3K) substitutions of Glu$_{573, 578, 579}$. Following exposure to clustered (+) or non-clustered (0) ephrin-A5 Fc, cleaved ephrin was recovered and analysed by Western Blot as described in FIG. 1c. Parallel anti-HA blots of whole-cell lysates reveal the expression levels of ADAM10 constructs.

D. Model of ADAM protein modules and cleavage mechanism. Left, schematic representation of ADAM proteinases protein domain organization; right, schematic representation of the proposed interactions and positioning of ADAM10, EphA3, and Ephrin-A5 between interacting cells, leading to controlled ephrin-cleavage.

E. Ephrin cleavage from the cell surface is blocked by overexpression of 3A-mutant ADAM10. HEK293 cells were co-transfected with (red-fluorescent) EphA3-diHcRed and either wt ADAM10, ADAM10 bearing alanine (3A) substitutions at Glu$_{573}$, Glu$_{578}$, and Glu$_{579}$, or dominant-negative ADAM10$_{AMP}$. These were then co-incubated with HEK293 cells expressing (green fluorescent) GFP-ephrin-A5 or GFP-ephrin-A2 for 40 min, fixed, and stained with anti-HA antibodies. Individual confocal images of GFP-ephrin-expressing cells (green), EphA3-diHcRed-expressing cells (red), anti-HA-ADAM10-staining (Alexa$^{647}$, blue), as well as merged images, are shown as indicated. Arrowheads indicate cleaved and internalised ephrin, arrows indicate ephrin aggregates at interacting cell surfaces. The percentage of EphA3- and HA-ADAM10 expressing HEK293 cells in contact with ephrin/HEK293 cells that internalised ephrin is shown in the right panel.

Figure 5:
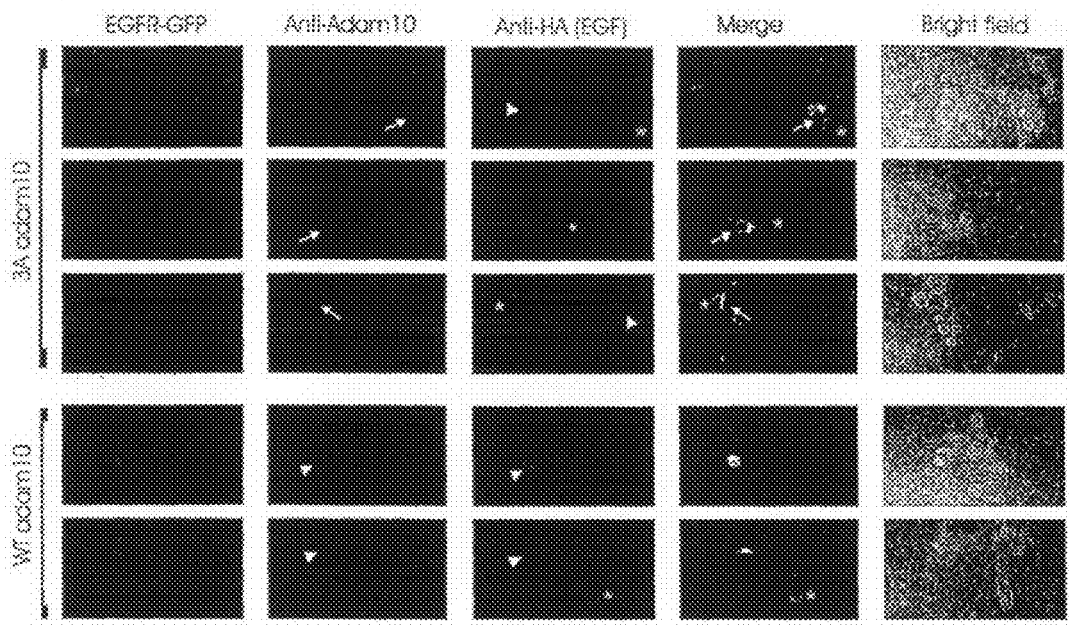

FIG. 5. Cleavage of cell surface pro-EGF by ADAM10 co-expressed with the EGF receptor requires the intact substrate recognition pocket of ADAM10. HEK293 cells transiently expressing EGFR-GFP and either wild type or 3A mutant ADAM10 (as indicated) were co-incubated with HEK293 cells expressing HA-tagged pro-EGF for 15 min. The cells were then washed, fixed and stained with antibodies against ADAM10 (Alexa$^{546}$, red) and HA (Alexa$^{647}$, cyan). Arrows indicate EGFR/3A Adam10-expressing cells unable to take up EGF from associated HA-pro-EGF expressing cells (stars); arrowheads indicate cells that have taken up EGF that over-express EGFR and wtAdam10 (bottom panels), or just EGFR (with endogenous Adam10), top panels.

FIG. 6. Fluorescence Energy Transfer (RET) analysis monitoring the formation of EphA3/ephrin-A5/ADAM10$_{D+C}$ complexes.

A) The proposed screening approach for inhibitors of the complex formation is based on a Homogeneous Time Resolved Fluorescence (HTRF™) Assay using a Eu$^{3+}$ chelate labeled donor and a XL665 labeled acceptor protein. Interactions between ADAM10 and its substrate, the EphA3/ephrinA5 complex are measured using (normalized) emission at 665 nm: the interaction brings the labels into proximity and triggers fluorescence resonance energy transfer (FRET), which initiates a chemical reaction cascade to produce an amplified fluorescent signal. Drugs or antibodies interfering with the interaction will weaken or abrogate the signal.

B) To illustrate the feasibility of the assay, the complex between XL665 labeled EphA3-Fc and ephrin-A5 was incubated with increasing concentrations of labeled ADAM10$_{D+C}$. The X axis shows the concentration of the complex while Y axis depicts the ratio of A665/A620, as a measure of the energy transfer between the two labels on EphA3 Fc and ADAM$_{D+C}$ (blue diamonds). Unlabelled ADAM10$_{D+C}$ at increasing concentrations was added to a constant concentration (320 nM) EphA3/ephrin-A5 Fc complex to demonstrate its capacity as competitive inhibitor of this interaction.

DETAILED DESCRIPTION OF THE INVENTION

The present invention arises, at least in part, from the discovery that ADAM10 associates constitutively with EphA3 receptor via an interaction with the EphA3 ligand-binding domain. Upon cell-cell contact, the formation of the high-affinity EphA3/ephrin-A5 complex creates a new binding site for the ADAM10 cysteine-rich domain, and the resulting interaction positions the ADAM proteinase domain in a conformation allowing the cleavage of ephrin-A5 from the ligand-expressing cells. Likewise, EphA3/ephrin-A2 complexes provide ADAM10 binding sites that facilitate ephrin-A2 cleavage. In a similar manner, the ADAM17 cysteine-rich domain binds a high-affinity complex between EphB4 or EphB2 and ephrin-B2, which is not recognised by ADAM10, indicating specificity of ADAM10 and ADAM17 for type A and type B ephrins, respectively. The molecular structure of the ADAM10 cysteine-rich and disintegrin domains containing the substrate-recognition and proteinase-positioning module was elucidated by X-ray crystallography. Structure-based mutagenesis and functional analysis of mutant ADAM proteins reveal that an acidic pocket, conserved between ADAM10 and ADAM17 and positioned within their respective cysteine-rich domains, forms a substrate-recognition site. Alteration of the substrate-recognition site, by mutation of critical surface residues, leads to loss of substrate recognition, thereby preventing ADAM10 from cleaving its substrate, in this case ephrin-A5 or ephrin-A2.

This provides a novel approach for controlling ADAM cleavage of a cell-bound receptor ligand, which exploits the unique recognition of a functional receptor/ligand complex by the ADAM metalloprotease. Apart from the ephrins the concept has implications for the regulation of cleavage of other cell membrane-bound ADAM10 or ADAM17 targets, including the ligands of the erbB family of receptors (EGF, HB-EGF, TGF-α, amphiregulin, betacellulin, epiregulin) and the TNF-receptor (TNF-α). Indeed, the present inventors have confirmed that ADAM10 mutated in the substrate-recognition site has a severely impaired ability to cleave cell surface pre-EGF.

Thus, in particular embodiments relating to Eph receptors and ephrins, the invention contemplates use of the surface pocket within the extracellular domain of ADAM10 and ADAM17 that mediates ephrin recognition and cleavage as a target for structure-based computational and high-throughput screens for small-molecule substrate-specific ADAM inhibitors. In particular, the surface residues Glu573, Glu578 and Glu579 lining the pocket of ADAM10 define specific interaction sites (as their mutation leads to abrogation of ADAM10 activity). Alternatively, the surface pocket and its recognition of receptor/ligand complexes can be used to screen for those monoclonal antibodies raised against the cysteine-rich domain that inhibit the interaction with ADAM substrates. Targeting the cleavage by ADAM10 of ephrin and erbB ligands could provide important therapeutic interventions of tumour development, invasion and metastasis, inflammatory disease and cardiac hypertrophy.

In other embodiments, the invention contemplates the design and/or screening of inhibitors of ADAM10 activity in cleavage of membrane-bound proteins. These include the chemokine ligands CXCL1 and CXCL16 and adhesion molecules L1 and CD44 which, like the ephrins, are involved in control of cell migration and/or adhesion. Other ADAM10/17 functions include shedding of the Notch ligand Delta and receptors such as erbB4, IL-6R and Notch, processing of cellular prion protein precursors and the Amyloid precursor protein (Seals & Courtneidge, 2003, supra).

A particular advantage provided by the present invention is that ADAM10 or ADAM17 inhibitors may be specifically designed to target cleavage of specific ADAM10 or ADAM17 substrates by interfering with substrate recognition and/or binding, thereby improving the specificity of therapies that target ADAM activity. This will provide a significant improvement over prior art strategies that rely on inhibitors of metalloprotease or ADAM catalytic activity per se, and therefore are unable to achieve selective cleavage of particular substrates of specific ADAM family members.

It will be appreciated that the invention described herein is preferably directed to human ADAM10 and/or ADAM17-mediated cleavage of substrate proteins expressed by, or derived from, human cells.

However, it will also be appreciated that the present invention is also readily extendible to ADAM10, ADAM17 and substrate proteins from other species due to substantial homology between mammalian species.

The human ADAM10 protein sequence comprising the critical residues is EKYGLEE (resides 573-579; SEQ ID NO:1).

The human ADAM17 protein sequence comprising the critical residues is EREQQLES (residues 583-590: SEQ ID NO:2).

For example, human ADAM10 residues Glu573, Glu578 and Glu579 are identical in bovine ADAM10.

In mouse, the corresponding residues are Glu574, Glu579 and Glu 580.

The amino acid residue numbering system used herein is based on sequences available under Genbank accession numbers: NM_001110 (human ADAM10), NM_174496 (mouse ADAM10), NM_007399 (bovine ADAM10), NM_003183 (human ADAM7) and NM_009615 (mouse ADAM17).

From the foregoing it will be appreciated that an ADAM10 or ADAM17 "substrate protein" is any protein that is proteolytically cleaved by ADAM10 or ADAM17 proteases.

Typically, ADAM10 and/or ADAM17 substrate proteins are "cell membrane-bound proteins", which according to the invention refer to a class of proteins that in their natural state, are expressed, associated, tethered or otherwise located at the cell surface.

This class of proteins includes cell surface receptors, membrane-bound ligands and adhesion molecules, although without limitation thereto.

It will be understood that the invention is not limited to cell membrane-bound proteins when present at the cell surface or in a membrane-bound form, but contemplates isolated forms of cell membrane-bound proteins that may be expressed in vitro or are present in any other artificial form or environment.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form.

By "protein" is meant an amino acid polymer. The amino acids may be natural or non-natural amino acids, D- or L-amino acids as are well understood in the art.

A "peptide" is a protein having no more than fifty (50) amino acids.

A "polypeptide" is a protein having more than fifty (50) amino acids.

Proteins inclusive of peptides and polypeptides may be conjugated to other moieties such as biotin and digoxigenin, enzymes such as horseradish peroxidase and alkaline phosphatase, radiolanthanides, fluorochromes and nucleic acids such as in peptide-nucleic acid complexes, although without limitation thereto.

The term "nucleic acid" as used herein designates single- or double-stranded mRNA, RNA, cRNA, RNAi and DNA inclusive of cDNA and genomic DNA.

A "polynucleotide" is a nucleic acid having eighty (80) or more contiguous nucleotides, while an "oligonucleotide" has less than eighty (80) contiguous nucleotides.

A "probe" may be a single or double-stranded oligonucleotide or polynucleotide, suitably labeled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™.

The invention provides a modified ADAM protease or an extracellular domain thereof that comprises one or more amino acid substitutions, additions, deletions and/or insertions.

Thus, in a particular form, the modified ADAM protease or extracellular domain thereof may be referred to as a "mutant".

The terms "mutant", "mutation" and "mutated" are used herein generally to encompass non-conservative amino acid substitutions, additions, deletions and/or insertions introduced into an ADAM protease or fragment thereof, that modify the ability of ADAM protease or said fragment to recognize, bind or otherwise interact with a substrate protein or a protein complex comprising the substrate protein.

Preferably, the modified ADAM10 or ADAM17 protease, or fragment thereof are incapable of recognising, binding and/or proteolytically cleaving a substrate protein, or have a reduced ability compared to the wild-type ADAM proteases.

The term "mutant" is also used herein in a similar manner to describe an isolated nucleic acid encoding a mutant ADAM10 or ADAM17 protease or an extracellular domain thereof.

In this regard, the present invention provides an isolated nucleic acid encoding a modified ADAM10 or ADAM17 protease, or fragment thereof.

In particular embodiments, the nucleotide sequence at positions 1733-1754 of Bovine ADAM10 GAGAAACATG-GCTTGGAGGAG (SEQ ID NO:3) has been modified to GCGAAACATGGCTTGGCGGCG (SEQ ID NO:4).

Alternatively, the nucleotide sequence at position 1745-1766 of mouse ADAM10 GAAAAGTATGACTTGGAG-GAG (SEQ ID NO:5) has been modified to GCAAAGTAT-GACTTGGCGGCG (SEQ ID NO:6).

Human ADAM 10 nucleotide sequence GAGAAATATG-GCTTAGAGGAG (SEQ ID NO:7) may be modified to GCGAAATATGGCTTAGCGGCG (SEQ ID NO:8).

Human ADAM17 nucleotide sequence GAGAGGGAA-CAGCAGCTGGAGTCC (SEQ ID NO:9) may be modified to GCGAGGGAACAGCAGCTGGCGGCC (SEQ ID NO:10).

The term "fragment" as used herein encompasses any portion, region or domain of an ADAM10 or ADAM17 protease extracellular domain.

In one particular form, the invention provides a fragment of an ADAM protease that binds or otherwise interacts with a substrate protein or a protein complex comprising the substrate protein and by competition with a full length or wild-type ADAM protease (e.g. an endogenous ADAM10 or ADAM17 protease) substantially reduces or prevents substrate recognition, binding and/or proteolytic cleavage.

In one particular embodiment, said fragment is capable of binding an ephrin such as ephrin-A5, ephrin-A2 or ephrin-B2, when present in a protein complex comprising an Eph receptor, such as EphA3 or EphB2/EphB4, respectively.

In another particular embodiment relating to ADAM10, the fragment is capable of binding an EGF-type ligand precursor such as pro-EGF or pro-amphiregulin.

In another particular embodiment relating to ADAM17, the fragment is capable of binding an EGF-type ligand precursor such as pro-Hb-EGF, pro-betacellulin or TGF-α.

Preferably, pro-Hb-EGF, pro-betacellulin or pro-TGF-α are in an isolated protein complex comprising the EGF-receptor erbB1.

In one form of these embodiments, said fragment is a cysteine-rich domain of human ADAM10 or human ADAM17 protease and, optionally, a disintegrin domain of an ADAM10 or ADAM17 extracellular domain.

Examples of a fragment having a cysteine-rich domain and a disintegrin domain are fragments comprising residues 483-646 of human ADAM10 or residues 501-644 of human ADAM17 (referred to herein as an ADAM10$_{D+C}$ or ADAM10$_{D+C}$ protein construct).

Examples of fragments having a cysteine-rich domain in the absence of a disintegrin domain are fragments comprising residues 552-646 of ADAM10 or residues 564-644 of ADAM17.

These fragments are respectively encoded by residues 2098-2382 of a human ADAM10 nucleic acid and residues 1873-2161 of a human ADAM17 nucleic acid.

It will be appreciated that an ADAM protease fragment may consist of a cysteine-rich domain of an ADAM10 or ADAM17 protease and, optionally, a disintegrin domain of an ADAM10 or ADAM17 extracellular domain.

It will also be appreciated that an ADAM protease fragment may consist essentially of an ADAM10 or ADAM17 protease and, optionally, a disintegrin domain of an ADAM10 or ADAM17 extracellular domain.

By "consist essentially of" is meant that the fragment further includes 1, 2 or 3 additional amino acid residues at an N- and/or C-terminus thereof.

The invention also provides a mutated fragment of an ADAM10 or ADAM17 protease having one or more amino acid substitutions in the cysteine-rich domain of the extracellular domain of ADAM10 or of ADAM17.

Amino acid substitutions may be conservative or non-conservative, as are understood in the art.

In particular embodiments relating to ADAM10, the one or more non-conservatively substituted amino acids are selected from the group consisting of a Glu573 substitution, a Glu578 substitution and a Glu579 substitution of human or bovine ADAM10.

In particular embodiments relating to human ADAM17, the one or more non-conservatively substituted amino acids are selected from the group consisting of a Glu583 substitution, a Glu589 substitution and a Ser590 substitution.

Preferably, the aforementioned residues in ADAM10 or ADAM17 are substituted by alanine.

In another embodiment, a "fragment" includes an amino acid sequence that constitutes less than 100%, but at least 10%, preferably at least 25%, more preferably at least 50% or even more preferably at least 75% of an isolated ADAM protease extracellular domain.

In yet another embodiment, a "fragment" is a small peptide, for example of at least 6, preferably at least 10 and more preferably at least 20 amino acids in length. Larger fragments comprising more than one peptide are also contemplated, and may be obtained through the application of standard recombinant techniques or synthesized using conventional liquid or solid phase synthesis techniques. Alternatively, peptides can be produced by digestion of a polypeptide of the invention with proteinases such as endoLys-C, endoArg-C, endoGlu-C and staphylococcus V8-protease. The digested fragments can be purified by, for example, high performance liquid chromatographic (HPLC) techniques.

It will be appreciated that shorter fragment (such as 15-50 amino acids long) may be useful in the preparation of antibodies as will be described in more detail hereinafter.

As used herein, "derivative" proteins of the invention are proteins which have been altered, for example by conjugation or complexing with other chemical moieties or by post-translational modification techniques as would be understood in the art.

Non-limiting examples of derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the polypeptides, fragments and variants of the invention. Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2,4,6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids.

Modified ADAM proteases and fragments of the invention (inclusive of fragments and derivatives) may be prepared by any suitable procedure known to those of skill in the art including chemical synthesis and recombinant DNA technology.

It will be appreciated that modified ADAM proteases and, in particular, fragments thereof consisting of up to about 100 amino acids, may be prepared by chemical synthesis, inclusive of solid phase and solution phase synthesis. Such methods are well known in the art, although reference is made to examples of chemical synthesis techniques as provided in Chapter 9 of SYNTHETIC VACCINES Ed. Nicholson (Blackwell Scientific Publications) and Chapter 15 of CURRENT PROTOCOLS IN PROTEIN SCIENCE Eds. Coligan et al., (John Wiley & Sons, Inc. NY USA 1995-2001).

Alternatively, a recombinant protein may be conveniently prepared by a person skilled in the art using standard protocols as for example described in Sambrook et al., MOLECULAR CLONING. A Laboratory Manual (Cold Spring Harbor Press, 1989), incorporated herein by reference, in particular Sections 16 and 17; CURRENT PROTOCOLS 1N MOLECULAR BIOLOGY Eds. Ausubel et al., (John Wiley & Sons, Inc. 1995-1999), incorporated herein by reference, in particular Chapters 10 and 16; and CURRENT PROTOCOLS IN PROTEIN SCIENCE Eds. Coligan et al., (John Wiley & Sons, Inc. 1995-1999) which is incorporated by reference herein, in particular Chapters 1, 5 and 6.

For example, the modified ADAM protease or fragment may be prepared as a recombinant protein by a procedure including the steps of:

(i) introducing an expression construct which comprises an isolated nucleic acid encoding the ADAM protease or fragment, operably linked to one or more regulatory nucleotide sequences in an expression vector into a host cell; and (ii) expressing the recombinant modified ADAM protease in said host cell from which the recombinant modified ADAM protease may be isolated.

In the context of the present invention it will be appreciated that in certain embodiments, an expression construct comprises a mutagenized nucleic acid encoding an ADAM10 or ADAM17 protease or fragment thereof, for the purposes of subsequent characterization of substrate binding.

In other embodiments, an expression construct comprises a nucleic acid encoding a modified ADAM10 or ADAM17 protease or fragment thereof that is incapable of binding a substrate protein, or has a reduced binding affinity compared to a corresponding wild-type ADAM10 or ADAM17 protease.

According to this embodiment, the recombinant modified ADAM10 or ADAM17 protease or fragment thereof may be subsequently purified, either alone or when complexed with a substrate protein, such as for use in structural analysis (e.g. X-ray crystallography, multiple-wavelength anomalous dispersion (MAD) or NMR), although without limitation thereto.

As generally used herein, a "genetic construct" is any artificially created nucleic acid that incorporates, and facilitates use of, a nucleic acid encoding ADAM10 or ADAM17 protease, a fragment thereof or mutant forms of these according to the invention.

Such constructs may be useful for bacterial propagation and/or amplification of the nucleic acid, nucleic acid mutagenesis and/or recombinant expression of an encoded protein.

As used herein, a genetic construct used for protein expression is referred to as an "expression construct", wherein the isolated nucleic acid to be expressed is operably linked or operably connected to one or more regulatory sequences in an expression vector.

An "expression vector" may be either a self-replicating extra-chromosomal vector such as a plasmid, or a vector that integrates into a host genome.

Preferably, the expression vector is a plasmid vector.

By "operably linked" or "operably connected" is meant that said regulatory nucleotide sequence(s) is/are positioned relative to the nucleic acid to be expressed to initiate, regulate or otherwise control expression of the nucleic acid.

Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, splice donor/acceptor sequences and enhancer or activator sequences.

Constitutive or inducible promoters as known in the art are contemplated by the invention and include, for example, tetracycline-repressible, ecdysone-inducible, alcohol-inducible and metal-inducible promoters. The promoters may be either naturally occurring promoters (e.g. alpha crystallin promoter, ADH promoter, human elongation factor α promoter and viral promoters such as SV40, CMV, HTLV-derived promoters), or synthetic hybrid promoters that combine elements of more than one promoter (e.g. SR alpha promoter).

In a preferred embodiment, the expression vector comprises a selectable marker gene. Selectable markers are useful whether for the purposes of selection of transformed bacteria (such as bla, kanR and tetr) or transformed mammalian cells (such as hygromycin, G418 and puromycin).

Suitable host cells for expression may be prokaryotic or eukaryotic, such as *Escherichia coli* (DH5α for example), yeast cells, SF9 cells utilized with a baculovirus expression system, CHO cells, COS, CV-1, Jurkat, PC12 and EK293 cells, without limitation thereto.

The expression vector may also include at least one additional amino acid sequence, such as an epitope tag or fusion partner (typically provided by the expression vector) so that the recombinant protein of the invention is expressed as a fusion protein with said fusion partner. An advantage of fusion partners is that they assist identification and/or purification of said fusion protein.

Well known examples of fusion partners include, but are not limited to, glutathione-S-transferase (GST), Fc and hinge portion of human IgG, maltose binding protein (MBP) and hexahistidine ($HIS_6$), which are particularly useful for isolation of the fusion protein by affinity chromatography. For the purposes of fusion protein purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system.

In some cases, the fusion partners also have protease cleavage sites, such as for Factor $X_a$ or Thrombin, which allow the relevant protease to partially digest the fusion protein of the invention and thereby liberate the modified receptor protein of the invention therefrom. The liberated modified receptor protein can then be isolated from the fusion partner by subsequent chromatographic separation.

Fusion partners according to the invention also include within their scope "epitope tags", which are usually short peptide sequences for which a specific antibody is available. Well-known examples of epitope tags for which specific monoclonal antibodies are readily available include c-myc, influenza virus hemagglutinin and FLAG tags.

Another fusion partner is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion polypeptide of the invention, or for isolating cells which express a fusion protein of the invention. Flow cytometric methods such as fluorescence activated cell sorting (FACS) are particularly useful in this latter application.

With regard to recombinant protein expression in general, standard protocols are provided in Sambrook et al., MOLECULAR CLONING. A Laboratory Manual (Cold Spring Harbor Press, 1989), incorporated herein by reference, in particular Sections 16 and 17; CURRENT PROTOCOLS 1N MOLECULAR BIOLOGY Eds. Ausubel et al., (John Wiley & Sons, Inc. 1995-1999), incorporated herein by reference, in particular Chapters 10 and 16; and CURRENT PROTOCOLS IN PROTEIN SCIENCE Eds. Coligan et al., (John Wiley & Sons, Inc. 1995-1999) which is incorporated by reference herein, in particular Chapters 1, 5 and 6.

Mutagenesis and Expression Screening

The present invention has arisen, at least in part, from an analysis of the substrate protein-binding properties of a mutagenized ADAM10 protease, or more particularly, an extracellular cysteine-rich domain and various mutants thereof.

Thus, in a particular aspect, the invention provides a method of producing an ADAM protease or fragment thereof that is incapable of recognizing, binding and/or proteolytically cleaving a substrate protein, or which has a reduced ability compared to a wild-type ADAM protease, said method including the steps of:

(i) introducing one or more amino acid substitutions into an ADAM10 or ADAM17 protease or fragment thereof, or into a nucleic acid encoding same to produce a modified ADAM10 protease or fragment thereof; and (ii) determining whether said modified ADAM10 or ADAM17 protease or fragment thereof is incapable of binding to and/or proteolytically cleaving a substrate protein, or which has a reduced ability compared to a wild-type ADAM10 or ADAM17 protease.

In a particular embodiment relating to ADAM10, the substrate protein is ephrin-A5, preferably when present in a protein complex comprising EphA3.

In another embodiment relating to ADAM10, the substrate protein is ephrin-A2, preferably when present in a protein complex comprising EphA3.

In yet another embodiment relating to ADAM17, the substrate protein is ephrin-B2, preferably when present in a protein complex comprising EphB2 or EphB4.

However, it will be appreciated that the present invention is also applicable to other cell surface receptors activated or otherwise modulated by ADAM10 or ADAM17 proteolytic cleavage. These include the ligands for the erbB receptor family (EGF, HB-EGF, TGF-α, amphiregulin, betacellulin, epiregulin) and the TNF-receptor (TNF-α), chemokine ligands CXCL1 and CXCL16 and adhesion molecules L1 and CD44, which are involved in control of cell migration and/or adhesion. Other ADAM10 functions include shedding of the Notch ligand Delta, as well as receptors such as erbB4 (HER4), IL-6R and Notch.

Mutations may be introduced into an ADAM protease or fragment thereof, such as by chemically synthesizing a modified protein, by chemical mutagenesis of an ADAM protease or fragment thereof, or by introducing one or more mutations into an encoding nucleic acid.

In certain embodiments, mutations are introduced into an isolated nucleic acid by a nucleotide sequence amplification technique.

Nucleic acid amplification techniques are well known to the skilled addressee, and include polymerase chain reaction (PCR) and ligase chain reaction (LCR) as for example described in Chapter 15 of Ausubel et al. supra; strand displacement amplification (SDA) as for example described in U.S. Pat. No. 5,422,252; rolling circle replication (RCR) as for example described in Liu et al., 1996, J. Am. Chem. Soc. 118 1587, International Publication WO 92/01813 and International Publication WO 97/19193; nucleic acid sequence-based amplification (NASBA) as for example described by Sooknanan et al., 1994, Biotechniques 17 1077; Q-β replicase amplification as for example described by Tyagi et al., 1996, Proc. Natl. Acad. Sci. USA 93 5395 and helicase-dependent amplification as for example described in International Publication WO 2004/02025.

As used herein, an "amplification product" refers to a nucleic acid product generated by nucleic acid amplification techniques.

A preferred nucleic acid sequence amplification technique is PCR.

Mutations may be introduced into nucleic acids by random or site-directed mutagenesis as are well known in the art. Non-limiting examples of nucleic acid mutagenesis methods are provided in Chapter 9 of CURRENT PROTOCOLS 1N MOLECULAR BIOLOGY, Ausubel et al., supra, Stemmer, 1994, Proc. Natl. Acad. Sci. USA 91 10747, Shafikhani et al., 1997, Biotechniques 23 304, Jenkins et al., 1995, EMBO J. 14 4276-4287 and Zaccolo et al., 1996, J. Mol. Biol. 255 589.

Mutagenesis kits are also commercially available, such as the Diversify™ random mutagenesis kit (Clontech).

In particular embodiments mutations include a change of the nucleotide sequence of bovine ADAM10 (accession number: NM_174496) from $_{1733}$GAGAAACATGGCTTGGAGGAG$_{1754}$ (SEQ ID NO: 3) to $_{1733}$CGAAACATGGCTTGGCGGCG$_{1754}$ (SEQ ID NO: 4) and of mouse ADAM10 (accession number NM_007399) from $_{1745}$GAAAAGTATGACTTGGAGGAG$_{1766}$ (SEQ ID NO: 5) to $_{1745}$GCAAAGTATGACTTGGCGGCG$_{1766}$ (SEQ ID NO: 6) and corresponding mutants in mouse ADAM17, accession #NM_009615.

Determination of mutations that affect ADAM protease binding to and/or cleavage of a substrate protein may be performed by a method including the steps of:

(A) purifying a recombinant modified ADAM10 or ADAM17 protein or fragment thereof; and (B) determining whether the modified ADAM10 or ADAM17 protein or fragment thereof is incapable of binding and/or cleavage of a substrate protein or at least has a reduced ability to bind and/or cleave the substrate protein.

Alternatively, mutated ADAM10 or ADAM17 proteins are overexpressed in receptor-expressing cells and altered capacity for the cleavage of GFP-tagged, cell-surface substrates is monitored by fluorescence microscopy.

Determination of substrate binding may be performed by any of a variety of techniques that measure protein-protein interactions, such as but not limited to immunoprecipitation or "pull-down" of protein complexes, BIAcore analysis including other surface plasmon resonance techniques, equilibrium dialysis, sedimentation and ultracentrifugation analysis, ELISA, ALPHA screen technology (Perkin Elmer), fluorescence microscopic analysis of the binding of fluorescent ligand derivatives to cells and the more traditional equilibrium radioligand binding measurements, although without limitation thereto.

Determination of substrate cleavage may be performed using any suitable ADAM protease activity assay. In a non-limiting example of ephrin-A5 and ephrin-A2, cleaved ephrin-A5 may be recovered with Protein A Sepharose-coupled EphA3-Fc and detected by Western blot, or its cleavage from the cell surface or synthetic beads and internalisation into EphA3-expressing cells monitored by fluorescence microscopy.

ADAM Modulator Design and Screening

The present invention has delineated critical domains and amino acid residues of ADAM10 and ADAM17 proteases that mediate the binding interaction with ephrins and their respective Eph receptors, and, hence, which are required for ADAM proteolytic cleavage of ephrin substrates.

Preferably, the amino acid residues of ADAM10 are selected from the group consisting of: Glu573, Glu578 and Glu579.

Preferably, the amino acid residues of ADAM17 are selected from the group consisting of: Glu583, Glu589 and Ser590.

Thus, the present invention contemplates use of the aforementioned protein domains and/or residues in the design and screening of molecules that modulate ADAM protease-mediated recognition, binding and/or proteolytic cleavage of substrate proteins, herein referred to as "ADAM protease modulators".

In particular, ADAM10 and ADAM17 modulators may be created by rational design based on structural analysis of ADAM10 and/or ADAM17 proteases, a C-terminal cysteine-rich fragment of the extracellular domain of ADAM10 and/or ADAM17, modified forms of these and protein complexes formed with cell surface proteins such as EphA3 or EphB4, although without limitation thereto.

Alternatively, ADAM modulators may be identified by screening of molecular libraries, inclusive of synthetic chemical libraries, combinatorial libraries, libraries of naturally occurring molecules and antibodies.

The term "mimetic" is used herein to refer to molecules that are designed to resemble particular functional regions of a protein or peptide, and includes within its scope the terms "agonist", "analogue" and "antagonist" as are well understood in the art.

The aforementioned mimetics, agonists, antagonists and analogues may be peptides, proteins such as antibodies (preferably monoclonal antibodies) or other organic molecules, preferably small organic molecules, with a desired biological activity and half-life.

These may be identified by way of screening libraries of molecules such as synthetic chemical libraries, including combinatorial libraries, by methods including but not limited to those described in Schneider, 2002, Curr. Med. Chem. 9 2095 which is directed to virtual combinatorial library design and screening, Nestler & Liu, 1998, Comb. Chem. High Throughput Screen. 1 113 and Kirkpatrick et al., 1999, Comb. Chem. High Throughput Screen 2 211.

It is also contemplated that libraries of naturally-occurring molecules may be screened by methodology such as reviewed in Kolb, 1998, Prog. Drug. Res. 51 185 or by approaches described in Eldridge et al., 2002, Anal. Chem. 74 3963, by way of example only.

More rational approaches to designing mimetics may employ computer assisted screening of structural databases, structural bioinformatic approaches, computer-assisted modelling, or more traditional biophysical techniques which detect molecular binding interactions, as hereinbefore described and as are well known in the art.

A recent review of structural bioinformatic approaches to drug discovery is provided in Fauman et al., 2003, Meth. Biochem. Anal. 44 477.

Computer-assisted molecular modelling and database searching is becoming increasingly utilized as a procedure for identifying and designing mimetics. Non-limiting examples of database searching methods which, in principle, may be suitable for identifying mimetics, may be found in International Publication WO 94/18232 (directed to producing HIV antigen mimetics), U.S. Pat. No. 5,752,019, International Publication WO 97/41526 (directed to identifying EPO mimetics) and van de Waterbeemd & Gifford, 2003, Nat. Rev. Drug Discov. 2 192 (dealing with in silico modelling of drug pharmacokinetics).

Other methods include a variety of biophysical techniques which may be used to identify and measure molecular interactions such as competitive radioligand binding assays, protein arrays, analytical ultracentrifigation, microcalorimetry, surface plasmon resonance and optical biosensor-based methods are provided in Chapter 20 of CURRENT PROTOCOLS IN PROTEIN SCIENCE Eds. Coligan et al., (John Wiley & Sons, 1997) which is incorporated herein by reference.

In a particular embodiment, design and/or screening of ADAM protease modulators is directed to producing an ADAM10 or ADAM17 protease inhibitor.

Thus, in one form this embodiment contemplates a method of identifying an inhibitor of ADAM10 or ADAM17 protease including the step of determining whether a candidate inhibitor molecule prevents, reduces or otherwise inhibits formation of a complex between an ADAM10 or ADAM17 protease fragment comprising a cysteine-rich domain of ADAM10 or ADAM17 protease, and a protein substrate of ADAM10 or ADAM17, wherein if the candidate molecule prevents, reduces or otherwise inhibits formation of the complex, it is identified as an inhibitor of ADAM10 or ADAM17 protease.

One particular method contemplated by the present invention utilizes Fluorescence Energy Transfer (FRET) analysis to monitor the formation of isolated protein complexes comprising an Eph, an ephrin and an ADAM10 or ADAM17 protease in the presence of a candidate inhibitor.

In this regard, screening or identification of inhibitors of complex formation is based on high-throughput homogeneous time resolved fluorescence (HTRF™) technology utilising donor and acceptor fluorescence labels that are conjugated to Fc-tagged proteins. An interaction between proteins brings the labels into proximity and triggers fluorescence resonance energy transfer (FRET), which initiates a chemical reaction cascade to produce an amplified fluorescent signal. An example of this assay is described hereinafter with reference to FIG. 6A, wherein a complex between EphA3-Fc and ephrin-A5 was incubated with increasing concentrations of Fc-tagged ADAM10$_{D+C}$, and the energy transfer between the two labels on EphA3 Fc and ADAM$_{D+C}$-Fc measured accordingly.

In particular embodiments, the candidate inhibitor is an antibody or a small organic molecule.

It will also be appreciated that ADAM protease inhibitor design and/or screening may utilize ADAM proteolytic cleavage of recombinant or synthetic substrate proteins as a "read-out" as well as, or as an alternative to, measurement of substrate binding.

Ephs and ephrins are both upregulated in a range of cancers, including breast, lung, colon, prostate, kidney carcinomas, malignant melanomas, neuroblastomas where they potentially promote both tumour growth (through angiogenesis), invasion and metastasis (through control of cell adhesion/repulsion). Likewise, ubiquitously expressed ADAM proteases are upregulated in several cancers, including breast and colon carcinomas and in neuroblastomas. Thus, one embodiment of the present invention contemplates ADAM10 and ADAM17 protease inhibitors that target the action of ADAM10 and ADAM17 on ephrin cleavage to thereby provide therapeutic intervention of tumour development, invasion and metastasis.

However, the region identified as regulating ADAM10 cleavage of ephrin-A5 or ephrin-A2 might have relevance not only for other ephrins, such as ephrin-B2, but also for other disease-related targets of ADAM10 and ADAM17.

Therefore, the present invention is not limited to designing and/or identifying ADAM10 inhibitors that target ephrin-A5 cleavage.

As previously described, ADAM10 and ADAM17 have been implicated in cleavage of a range of membrane-bound proteins including also the trans-membrane anchored pro-forms of EGF, HB-EGF, TGF-α, amphiregulin, betacellulin and epiregulin. These EGF receptor ligands have well-established functions in promoting proliferation and motility of tumour cells, in particular supporting the autocrine growth of several cancers (Steals & Courtneidge, 2003, Genes & Dev. 17 7-30).

ADAM10 and ADAM17-mediated cleavage of EGF receptor ligands is also directly involved in the 'transactivation of the EGF receptor by G-protein-activated receptors, a crosstalk with important implications in cancer cell proliferation (Fisher et al., 2003, Biochemical Society Transactions 31 1203-1208), and which is the underlying mechanism in cardiac and gastrointestinal hypertrophy. Shedding (cleavage) by ADAM10 converts cell-membrane-associated pro-EGF into the active, EGF-receptor-binding form of EGF (as illustrated in example 6)

Importantly, ADAM17 proteolytically converts pro-TNF-α into the active, TNF-receptor-binding, mature form. The role of ADAM17 is of therapeutic relevance as active TNF-α is a pro-inflammatory cytokine directly involved in inflammatory diseases such as rheumatoid arthritis and cachexia. ADAM10 and ADAM17 are also responsible for the release of the chemokine ligands CXCL1 and CXCL16 and the adhesion molecules L1 and CD44 involved in the control of cell migration and/or adhesion (Seals & Courtneidge, 2003, supra). Other ADAM10 functions that may be targeted by ADAM10 modulators include shedding of the Notch ligand Delta, as well as receptors such as erbB4, interleukin-6 receptor and Notch.

Pharmaceutical Compositions and Treatment Methods

The invention provides a pharmaceutical composition comprising a modulator of ADAM10 and/or ADAM17 and a pharmaceutically-effective carrier, diluent or excipient.

The invention also provides a method of a prophylactically or therapeutically treating a disease or condition responsive to modulation of ADAM10 and/or ADAM17 activity in an animal, said method including the step of administering a modulator of ADAM10 and/or ADAM17 to said animal to thereby modulate ADAM10 activity.

Preferably, said modulator inhibits, reduces or prevents ADAM10 and/or ADAM17 recognition, binding and/or proteolytic cleavage of one or more cell surface proteins of said animal.

In particular embodiments, the disease or condition responsive to modulation ADAM10 and/or ADAM17 activity is tumour development, invasion and/or metastasis.

In further embodiments, the disease or condition responsive to modulation ADAM10 and/or ADAM17 activity are inflammatory conditions, such as rheumatoid arthritis and cachexia.

In further embodiments, the disease or condition responsive to modulation ADAM10 and/or ADAM17 activity is hypertrophy of the heart.

It will be appreciated that ADAM protease modulators of the invention may be used to target binding and/or cleavage of specific ADAM protease substrates (including but not limited to the Eph/ephrin system), thereby improving therapies that target ADAM protease activity. This should be compared with prior art strategies that rely on inhibitors of ADAM protease catalytic activity per se, which are unable to selectively target cleavage of particular ADAM protease substrates and thereby affect other types of metallo-proteases and therefore cannot be used to selectively inhibit ADAM10 or ADAM17 activity.

This is a particular problem due to the broad range of substrate proteins cleaved by ADAM and related proteases and hence the broad range of biological activities regulated by these, a problem that has resulted in rather disappointing outcomes of previous clinical trials.

In particular embodiments, the invention relates to preventing, inhibiting or delaying tumour cell metastasis through inhibition of ephrin cleavage by ADAM10 or ADAM17.

The effect of inhibition of ephrin cleavage by ADAM10 or ADAM17 protease and tumour cell metastasis may be achieved via decreased cell-cell repulsion and/or by reduced cell motility due to Eph/ephrin and/or EGF receptor signalling.

In light of the foregoing, it will be appreciated that tumour cell metastasis may be manipulated at various levels, including tumor cell spreading from the original site, colonisation of new tumor sites and neovascularisation according to the cell type concerned.

Non-limiting examples of such tumour cells include leukemias and lymphomas, lung and colon cancer, neuroblastoma, brain, renal and kidney tumours, prostate cancers, sarcomas and melanoma.

For a more comprehensive review of potentially relevant tumours the skilled person is directed to Nakamoto & Bergemann, 2002, Microsc. Res. Tech. 59 58-67, Wimmer-Kleikamp & Lackmann, 2005, IUBMB Life 57 421-431 and Fischer et al., 2003, Biochem Soc Trans, 2003, 31 1203-8.

Modulators of ADAM10 or ADAM17 protease may be identified, screened, designed or otherwise produced as hereinbefore described.

In one particular embodiment, an inhibitor of ADAM10 is an ADAM10 protease fragment that consists essentially of a cysteine-rich domain of ADAM10 protease extracellular domain, but is catalytically-inactive.

For example, an ADAM10 protease fragment consisting essentially of residues 552-646 of ADAM10 protease would bind a substrate such as ephrin-A5 complexed with EphA3, but would not proteolytically cleave the substrate, thereby acting as a competitive inhibitor of endogenous ADAM10.

In another particular embodiment, an inhibitor of ADAM17 is an ADAM17 protease fragment that consists essentially of a cysteine-rich domain of ADAM17 protease extracellular domain, but is catalytically-inactive.

For example, an ADAM17 protease fragment consisting essentially of residues 564-644 of ADAM17 protease would bind a substrate such as ephrin-B2 complexed with EphB2 or EphB4, but would not proteolytically cleave the substrate, thereby competing with endogenous ADAM17 protease.

In yet another particular embodiment, the modulator is a small molecule inhibitor of ADAM10 or ADAM17 or an inhibitory antibody.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference.

Any safe route of administration may be employed for providing a patient with the composition of the invention. For example, oral, rectal, parenteral, sublingual, buccal, intravenous, intra-articular, intramuscular, intra-dermal, subcutaneous, inhalational, intraocular, intraperitoneal, intracerebroventricular, transdermal and the like may be employed. Intra-muscular and subcutaneous injection is appropriate, for example, for administration of immunotherapeutic compositions, proteinaceous vaccines and nucleic acid vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Compositions of the present invention suitable for oral or parenteral administration may be presented as discrete units such as capsules, sachets or tablets each containing a predetermined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

The methods and compositions of the invention may be applicable to any animal in which ADAM10, ADAM17 or their othologues, are present.

In particular embodiments, the animal is a mammal including but not limited to humans, performance animals (such as horses, camels, greyhounds), livestock (such as cows, sheep, horses) and companion animals (such as cats and dogs).

In other embodiments, non-mammalian vertebrates are contemplated, including but not limited to poultry and other avians.

Antibodies

The invention also provides an antibody raised against, or capable of binding, a substrate recognition site within a cysteine-rich domain of an ADAM protease.

Suitably, the antibody binds with high affinity to the surface pocket within the cysteine-rich extracellular domain of wild-type ADAM10 or ADAM17, thereby preventing, inhibiting or reducing the binding or interaction of this recognition site to ADAM10 or ADAM17 substrates, to thereby block or inhibit substrate cleavage.

Suitably, the substrate recognition site is in a cysteine-rich domain of an ADAM protease comprising residues 552-646 of ADAM10 protease or a cysteine-rich region comprising residues 564-644 of ADAM17 protease. or against the modified ADAM protease or fragment thereof of the first aspect.

In another embodiment, the antibody is raised against, or capable of binding, a modified or mutated ADAM protease or fragment thereof.

In such an embodiment, the antibody preferably has a higher affinity for the modified or mutated ADAM protease than for a wild-type ADAM protease.

Such antibodies may be useful for discriminating between modified or mutated ADAM proteases and corresponding wild-type ADAM proteases, for example.

Antibodies of the invention may be polyclonal or preferentially monoclonal. Well-known protocols applicable to antibody production, purification and use may be found, for example, in Chapter 2 of Coligan et al., CURRENT PROTOCOLS IN IMMUNOLOGY (John Wiley & Sons NY, 1991-1994) and Harlow, E. & Lane, D. Antibodies: A Laboratory Manual, Cold Spring Harbor, Cold Spring Harbor Laboratory, 1988, which are both herein incorporated by reference.

Generally, antibodies of the invention bind to or conjugate with a polypeptide, fragment, variant or derivative of the invention. For example, the antibodies may comprise polyclonal antibodies. Such antibodies may be prepared for example by injecting a polypeptide, fragment, variant or derivative of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, supra, and in Harlow & Lane, 1988, supra.

Instead of polyclonal antibodies, monoclonal antibodies may be produced using a standard method, as for example described in an article by Köhler & Milstein, 1975, Nature 256, 495, which is herein incorporated by reference, or by more recent modifications thereof as for example, described in Coligan et al., CURRENT PROTOCOLS IN IMMUNOLOGY, supra by immortalizing spleen or other antibody producing cells derived from a production species which has been inoculated with one or more of the polypeptides, fragments, variants or derivatives of the invention.

In particular the invention includes inhibitory antibodies that by binding to the substrate recognition surface pocket within the cysteine-rich extracellular domain prevent the recognition and cleavage of ADAM10 and/or ADAM17 substrate proteins.

The invention also includes within its scope antibodies which comprise Fc or Fab fragments of the polyclonal or monoclonal antibodies referred to above. Alternatively, the antibodies may comprise single chain Fv antibodies (scFvs) against the ADAM10 and/or ADAM17 proteins of the invention. Such scFvs may be prepared, for example, in accordance with the methods described respectively in U.S. Pat. No. 5,091,513, European Patent No 239,400 or the article by Winter & Milstein, 1991, Nature 349 293, which are incorporated herein by reference.

Labels may be associated with an antibody of the invention, or antibody fragment, as follows:

(A) direct attachment of the label to the antibody or antibody fragment;

(B) indirect attachment of the label to the antibody or antibody fragment; i.e., attachment of the label to another assay reagent which subsequently binds to the antibody or antibody fragment; and (C) attachment to a subsequent reaction product of the antibody or antibody fragment.

The label may be selected from a group including a chromogen, a catalyst, an enzyme, a fluorophore, a chemiluminescent molecule, a lanthanide ion such as Europium ($EU^{34}$), a radioisotope and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes useful as labels is disclosed in U.S. Pat. Nos. 4,366,241, 4,843,000, and 4,849,338, all of which are herein incorporated by reference. Enzyme labels useful in the present invention include, for example, alkaline phosphatase, horseradish peroxidase, luciferase, β-galactosidase, glucose oxidase, lysozyme, malate dehydrogenase and the like. The enzyme label may be used alone or in combination with a second enzyme in solution.

The fluorophore may be, for example, fluorescein isothiocyanate (FITC), Alexa dyes, tetramethylrhodamine isothiocyanate (TRITL), allophycocyanin (APC), Texas Red, Cy5, Cy3, or R-Phycoerythrin (RPE) as are well known in the art.

So that the present invention may be more readily understood and put into practical effect, the skilled person is referred to the following non-limiting examples.

EXAMPLES

Expression Constructs

Mutations were introduced into mADAM10ΔMP-HA and full length bADAM10-HA constructs by site-directed mutagenesis (Quikchange XL, Stratagene). EphA3 ECD deletion mutants were produced by ligating the soluble ECD mutants described previously (Lackmann et al.; 1998, J Biol. Chem. 273 20228-20237) to the EphA3 transmembrane and cytoplasmic domains. The EphA3 Δcyto and ΔPDZb constructs were produced by introduction of stop codons at $Y_{570}$ and $K_{997}$, respectively. Fc fusion proteins of the ephrin-A5 and EphA3 extracellular domains fused to the hinge and Fc region of human IgG1 were produced as described (Lackmann et al., 1997, J Biol. Chem. 272 16521-16530). Myc-tagged ephrinA5 and GFP-ephrinA5 were constructed based on published ephrin-A2 constructs (Hattori et al., 2000, supra). EphA3-diHcRed was constructed by substitution of the GFP in EphA3-GFP (Wimmer-Kleikamp et al., 2004, J. Cell. Biol. 164 661-6) with a tandem repeat of HcRed (Rocks et al., 2005, Science 307 1746-52). The EGFP-tagged EGF receptor and N-terminal HA-tagged pro-EGF constructs used in our examples (FIG. 6) have been published previously (Clayton et al., 2005, J. Biol. Chem. 280 30392; Le Gall et al., 2003, J. Biol. Chem. 278 45255).

For the structural and in vitro binding assays, the sequence encoding the bovine Adam10 disintegrin and cysteine-rich domains (residues 455-646) was subcloned as an Fc-fusion into a modified pcDNA3.1 vector (Invitrogen). A thrombin cleavage site was engineered at the C-terminal end of the gene followed by the Fc domain. The N-terminus of the protein was fused to a prolactin signal sequence. The protein was expressed in stably-transfected human embryonic kidney293 (HEK293) cells and extracted from the medium using protein-A Sepharose (Amersham). The Fc tag was removed by thrombin cleavage and ADAM10$_{D+C}$ was purified to homogeneity on by gel filtration chromatography. Site directed cluster mutants of the protein were generated by two stage PCR thereby changing Glu573 Glu578 and Glu579 to alanines or Arg525, Asp526 and Asp527 to alanines. Deletion mutants of ADAM10 encompassing the disintegrin domain (residues 455-570) and the cysteine-rich domain (residues 571-646) were generated by PCR. The fragments were cloned into the same expression vector. The clones were sequenced for the presence of unwarranted mutations and purified in the same fashion as the wild type ADAM10$_{D+C}$.

ADAM10 Knockdown by RNA Interference

EphA3/HEK293 cells were transfected using Lipofectamine 2000 (Invitrogen) with ADAM10 specific siRNA duplexes 5'UGGGCAAUGUGCAGGUUCUTT3' (SEQ ID NO:11) (SKI-RSI-7722, Sloan Kettering Cancer Centre HTS core facility) or a mix of 5'AAUGAAGAGGGACACUUC-CCUdTdT3' (SEQ ID NO:12) and 5'AAGUUGCCUCCUC-CUAAACCAdTdT3' (SEQ ID NO:13) (Fischer et al., 2003, Mol.Cell.Biol. 24 5172-83) at 40 nM for 48 h prior to analysis. Parallel cell cultures were transfected with a control siRNA at the same concentration. Specific ADAM10 silencing was confirmed by RT-PCR analysis, by staining of cells with an anti-ADAM10 mouse monoclonal antibody and by anti-ADAM Western blot of ADAM10 immunoprecipitates.

Cell Manipulations, Immunoprecipitation and Western Blotting

Cells were cultured in DME/10% FCS and transfected with Lipofectamine 2000 (Invitrogen), and in some experiments treated with the metalloprotease inhibitors 1,10-O-Phenanthroline (OPN, 4h, 1 mM; Mumm et al., 2000, Mol. Cell. 5 197-206) and TAPI1 (1h, 50 µM; Yan et al., 2002, J Cell Biol. 158 221-6). HEK293 cells were transfected with EphA3 (Wicks et al., 1992, Proc. Natl. Acad. Sci. USA 89 1611-1615) or ephrin-A5 (Winslow et al., 1995, Neuron 14 973-81; Lackmann et al., 1996, Proc. Natl. Acad. Sci. USA 93 2523-2527) in pEfBos vectors containing puromycin or gentamycin resistance genes, respectively and stable EphA3/HEK293 or ephrin-A5/HEK293 clones derived accordingly. Serum-starved cells were stimulated (10 min) with 1.5 ug/ml pre-clustered ephrinA5-Fc and harvested, as described previously. Immunoprecipitation was with anti-EphA3 mAb IIIA4 (Boyd et al., 1992, J Biol. Chem. 267 3262-3267. or anti-HA mAb 3F10 (Roche) conjugated to beads, and Western blotting was performed using anti-ADAM10 (Biogenesis, UK), anti-ephrinA5 (R&D Systems) and anti-ephA3 (Lackmann et al., 1997, supra) antibodies.

Production of Alexa-labelled ephrinA5-Fc beads and confocal microscopy on an Olympus FluoView 500 microscope equipped with HeCd (442 nm), Ar-ion (488 nm), HeNe (543 nm) and HeNe (633 nm) lasers were performed as described previously (Wimmer-Kleikamp et al., 2004, supra). To monitor ADAM10-mediated cleavage during cell-cell interactions, ephrin-A5/HEK293 cells incubated (30 min) under gentle agitation on a semi-confluent monolayer of EphA3/HEK293 cells, whereby one of either cell line had been transfected to over-express mADAM10ΔMP-HA. Following aspiration of non-adherent cells, remaining cells were analysed for expressed proteins with mouse anti-EphA3 monoclonal antibodies (IIIA4), and following fixation (4% parformaldehyde) with rat anti-HA (Roche) and goat anti-ephrinA5 (R&D Systems) antibodies and appropriate, Alexa-labelled secondary antibodies. During confocal microscopy images of Alexa$^{488}$, Alexa$^{546}$, Alexa$^{647}$, and Hoechst fluorescence were collected sequentially to minimise "bleed-through" from spectral overlap. Confocal images were processed using analySIS (Soft Imaging System, Muenster, Germany) and assembled into figures using Coral draw.

In Vitro Binding Assay

Pull-down experiments were done as follows: ADAM10$_{D+C}$, ADAM17$_{D+C}$ w.t. or the alanine mutants (~15 µg) were incubated with Fc-tagged ectodomains of Eph-A3, EphB2, EphB4 and ephrin-A2, ephrin-A5, ephrin-B2 (R&D systems) at 4° C. for 30 min in 500 µL of binding buffer containing 10 mM HEPES (pH 7.4), 150 mM NaCl and 0.05% of Triton X-100. To test binding to the preformed EphA3/ephrin-A5 complex, 5 µg of the untagged ephrin-A5 was incubated with Fc tagged EphA3 for 30 min at 4° C. followed by the addition of ADAM10. The proteins were incubated for an additional 30 min., when Protein-A-Sepharose (Amersham) beads were added to the reaction mixture and shaken at 4° C. for 2h. The beads were then harvested by centrifugation, washed once with 500 µl of binding buffer and the bound proteins were separated on a 10-20% gradient polyacrylamide gel. The binding of the individual ADAM domains was carried out likewise using 15 µg of the disintegrin and 8 µg of the cysteine-rich domain.

Crystallization, Data Collection and Structure Determination

ADAM-10$_{D+C}$ was concentrated to 24 mg/ml in a buffer containing 10 mM HEPES pH 7.4 and 150 mM NaCl. The protein was crystallized in a hanging drop by vapor diffusion at room temperature against a reservoir containing 0.2 M ammonium sulfate and 30% polyethylene glycol 4000 (Hampton research). Sizable crystals (I4$_1$32 space group) grew after two months, but could be reproduced in two to three days with streak seeding. For heavy-metal derivatization, crystals were soaked in mother liquor, containing 1 mM auric chloride and frozen with 20% glycerol as cryoprotectant.

The structure was determined by MAD phasing. A 'peak' and 'remote' wavelength datasets were collected on an ADSC Quantum 210 CCD detector at CHESS line F2. Oscillation photographs were integrated, merged and scaled using DENZO and SCALEPACK (Otwinowski, Z., Minor, W., *Processing of X-ray diffraction data collected in oscillation mode*, in Methods in Enzymology, J. C. W. Carter, & R. M. Sweet Eds., Editor. 1997, Academic Press: New York. p. 307-326). Subsequent calculations were done with autoSHARP and the CCP4 program suite (Project, 1994, Acta Crystallogr., 1994. D 50 760-763), autoSHARP was used to identify the location of two distinct gold atoms, as well as to refine their position and occupancy for phase calculations. Density modification with DM improved the two-wavelength gold-derivative MAD maps that proved to be of sufficient quality to trace the main chain unambiguously. Refinement proceeded with iterative rounds of model adjustments (Jones et al., 1991, Acta Crystallogr. 47 110-9) molecular dynamics, and energy minimization in CNS (Brunger et al., 1998, Acta Crystallogr D Biol Crystallogr. 54 905-21).

The first model is refined at 2.9 Å resolution to R and free R values of 27.2% and 31.2% respectively. No electron density was observed for the first 39 N-terminal residues of the expression construct, as well as residues 584-590.

In light of the now available Eph/ephrin crystal structures, and the fact that the ephrin/ADAM10 interactions were shown to involve the receptor-binding ephrin domain and extracellular ADAM10 regions C-terminal to the proteinase domain, it seemed to us that a topological arrangement where the functional ADAM10 is located on the Eph-, rather than the ephrin-, expressing cells would be much more favourable for efficient cleavage. We therefore investigated in detail the potential ADAM10 interactions with EphA3 and its high-affinity ligand ephrin-A5 and the regulation of the ADAM10-mediated ephrin-A5 cleavage.

Initially, we investigated whether ADAM10 interacts with either EphA3 or ephrin-A5 on the cell surface and how these interactions are affected upon Eph/ephrin complex formation. Endogenous ADAM10 co-immunoprecipitated with EphA3 in cell lysates of stably EphA3-transfected HEK293 cells (EphA3/HEK293) and EphA3-positive LiBr melanoma cells, but not in lysates of parental (untransfected) HEK293 cells (FIG. 1A). Blocking of the anti-ADAM10 antibodies during immunoblot analysis, by pre-incubation with recombinant ADAM10$_{\Delta MP}$, reduced the ADAM10-associated bands to background (Δ in FIG. 1a), confirming its specificity. Eph/ADAM10 co-immunoprecipitation was increased in cells that had been exposed to pre-clustered ephrinA5-Fc or ephrinA2-Fc. EphA3 also co-immunoprecipitated with transiently-expressed, HA-tagged ADAM10 lacking the MetalloProtease domain ADAM10$_{\Delta MP}$ (discussed in Hattori et al., 2000, Science 289, 1360-65). By contrast, a parallel experiment revealed that ADAM10ΔMP did not interact with cell-surface ephrin-A5 in HEK293 cells stably expressing ephrin-A5 (ephrinA5/HEK293) (FIG. 1b).

Furthermore, using the same EphA3/HEK293 cells, we determined that pre-clustering of ephrin-A5-Fc was required to trigger effective ephrin cleavage (FIG. 1c) and internalisation (FIG. 1d), confirming the hypothesis that ephrin cleavage and Eph activation are linked. Cleavage and internalisation were inhibited by the metalloprotease inhibitor 1,10-O-Phenanthroline (OPN, used under conditions that maintain cell viability) and TAPI (FIG. 1d, II, III), consistent with their dependence on the activity of a metalloprotease such as ADAM10. In agreement, exogenous expression of dominant-negative ADAM10$_{\Delta MP}$ effectively blocked ephrin cleavage and internalisation, while ephrin internalisation progressed unhindered into the cells that remained untransfected (FIG. 2 E, F; the arrowheads indicate a cell, which has undetectable expression of exogenous ADAM10$_{\Delta MP}$).

To identify the EphA3 protein module interacting with ADAM10, expression constructs encoding wild-type (w/t) EphA3, or EphA3 lacking the globular ligand binding domain (LBD, ephA3 exons I-III) (Himanen & Nikolov, 2003, supra; Lackmann et al., 1998, supra) or portions of the cytoplasmic domain, were co-transfected together with ADAM10$_{\Delta MP}$ into HEK293 cells. Notably, constitutive and ephrin-A5-enhanced interactions between ADAM10 and EphA3 were abrogated by deletion of the globular ligand binding domain (FIG. 1e), while strong binding was retained in EphA3 mutants lacking the C-terminal PDZ-binding domain (FIG. 1e) or the whole cytoplasmic domain (EphA3Δcyto, not shown), suggesting the EphA3 LBD as providing the essential ADAM10 binding interface.

We next set out to determine which region of ADAM10 is responsible for interaction with EphA3. ADAMs have a multi-domain extracellular region (FIG. 3a, left) including an N-terminal pro-sequence that is removed to activate the protease, followed by a protease, a disintegrin, and a cysteine-rich domain (Primakoff, 2000, Trends Genet. 16 83-7). While the protease domain is not necessary for ADAM10-ephrin interaction, the disintegrin and cysteine-rich domains are involved in protein interactions mediating cell adhesion and are essential for ADAM specificity (Smith et al., 2002, J. Cell Biol. 159 893-902; Reddy et al., 2000, J. Biol. Chem., 275 14608-14614).

To test their contribution in Eph/ephrin interactions we used a recombinant, ADAM10$_{D+C}$ protein encompassing these two domains (residues 455-646), to assess binding to soluble Eph- and ephrin-Fc fusion proteins that were captured with Protein-A Sepharose. In agreement with previous work ADAM10$_{D+C}$ bound to ephrin-A2 and ephrin-A1 but not to ephrin-A5, or to any of the other ephrins tested (FIG. 2a). Likewise, no interaction was seen with the ectodomain of EphA3 (FIG. 2b), or any of the other Ephs tested (EphA2, -A4, -B1, -B2, — data not shown). However, ADAM10$_{D+C}$ readily bound and formed a stable complex when incubated simultaneously with both EphA3 and ephrin-A5. The use of single-chain ephrin-A5 lacking the Fc domain in these experiments, allowed us to capture selectively EphA3-bound ephrin, revealing that the presence of ADAM10$_{D+C}$ in the complex notably increased EphA3-bound ephrin-A5 (FIG. 2b: lanes 6&8; d: lanes 11&12; see also FIG. 4a), likely due to increased stability of the EphA3/ephrin-A5 interaction in this ternary complex. Analysis of further ADAM10 truncations revealed that its interaction with the EphA3/ephrin-A5 complex was mediated by the cysteine-rich domain which, in contrast to the disintegrin domain, bound to the EphA3/ephrinA5 complex on its own (FIG. 2c), and again increased the amount of complexed ephrin-A5. Performing the same Protein-A capture of EphB4/ephrin-B2 Fc complexes with ADAM10$_{D+C}$ revealed little or no association of ADAM10 to this EphB/ephrin-B complex (FIG. 2d). By contrast, when the ADAM17 disintegrin and cystein-rich domains (ADAM17$_{D+C}$) were tested, we observed its binding to EphB4-Fc, ephrin-B2-Fc and their high-affinity complex (FIG. 2e), as well as to the EphB2/ephrin-B2 complex (FIG. 2f). This suggests, that similar to the preferential cleavage of different EGF-receptor ligands by either ADAM10 or ADAM17 (EGF and betacellulin are cleaved by ADAM10; HB-EGF, TGF-α and amphiregulin are cleaved by ADAM17: Blobel, 2005, Nature Rev. Mol. Cell Biol. 6 1-12), ADAM10 preferentially recognises A-type Eph/ephrin complexes, while ADAM17 recognises EphB/ephrin-B complexes.

To gain further insight into the molecular architecture of the ADAM10 region mediating the Eph/ephrin interaction, we crystallized ADAM10$_{D+C}$ and determined its structure using X-ray crystallography, with the multiple-wavelength anomalous dispersion (MAD) method. The final model is refined at 2.9 Å to an R-factor of 27.2 (R$_{free}$ of 31.2) with tightly restrained temperature factors and good stoichiometry.

The ADAM10 disintegrin and cys-rich domain fold in a continuous elongated and curved structure which extends approximately 75 Å in length (FIG. 3). It has a relatively low secondary structure content, with just four short beta strands in the disintegrin domain (yellow on FIG. 3b), and four short strands and 3 short helices in the cys-rich domain (green on FIG. 3b). Small hydrophobic cores are present in the cys-rich domain and at the interface between the two domains, but the overall structure is mainly stabilized by a series of disulfide bonds. Indeed all of the cysteine residues present in the refined model are paired in a total of 10 disulfide bridges.

Comparison of ADAM10$_{D+C}$ with the FSSP structure database (Holm & Sander, 1998, Nucleic Acids Res. 26 316-9) reveals weak structural homology of the disintegrin domains of ADAM10 and the blood coagulation inhibitor (1fvl; Senn & Klaus, 1993, J. Mol. Biol. 232 907-925), while the ADAM10 cys-rich domain has a new and unique fold. The N-terminal disintegrin domain spans ADAM10 residues 493-569. The preceding 20 residues are also predicted to be part of this domain, but are disordered in our structure. The disintegrin domain contains six disulfide bonds, five of which (Cys495-Cys515; Cys503-Cys-511, Cys510-Cys536, Cys530-Cys562, Cys555-Cys567) are topologically identical to the disulfide bonds in blood coagulation inhibitor, while one (Cys524-Cys543) is distinct. Indeed, the disintegrin domain of ADAM10 can be superimposed on the disintegrin domains of trimestatin and the blood coagulation inhibitor with root-mean square deviations between α-carbon positions of 1.5 and 2.0 Å respectively, for a total of 50 directly equivalent residues sharing approximately 30% sequence identity (FIG. 3c).

The ADAM10 C-terminal cysteine-rich domain (residues 552-646) packs against the disintegrin domain via a mini hydrophobic core forming a continuous structure that seems to have little inter-domain flexibility. The cys-rich domain has a novel αlp fold stabilized by 4 conserved disulfide bonds: Cys572-Cys598, Cys580-Cys607, Cys597-Cys582 and Cys594-Cys639. It contains two β sheets: a larger one composed of the three N-terminal β strands that packs against the 3 α helices; and a smaller one composed of the two C-terminal β strands. The first α helix of the cysteine rich domain also packs against the C-terminal β sheet of the disintegrin domain. A long surface loop, located on the side opposite to the interface with the disintegrin domain is partially disordered, and six of its residues (584-590) were not included in the final model.

ADAM10$_{D+C}$ with its elongated form presents an extensive molecular surface (~10,000 Å$^2$) for potential interactions with other proteins, such as ADAM substrates. A schematic representation of this surface, colored in accordance with its electrostatic potential, is presented in FIG. 3d. Interestingly, while ADAM10$_{D+C}$ has an overall neutral charge, there is a relatively large negatively-charged pocket on one side of the cys-rich domain. The negative electrostatic surface potential results from the proximity of several solvent-exposed acidic residues, including Glu573 and Glu578 at the entrance and Glu579 inside the cavity (FIG. 3e). In addition, there are several hydrophobic residues both at the entrance (Phe635, Pro628, Pro631) and lining the bottom of the pocket (Val596, Leu626), suggesting that it might represent a protein-interaction interface.

To test whether this pocket indeed represents the substrate-binding site, assigned by our in-vitro binding experiments (FIG. 2c) to the cys-rich domain, we mutated Glu573, Glu578 and Glu579 to neutral alanines (ADAM10$_{D+C}$[EEE-A]). We also mutated, in a similar fashion, an RDD-like sequence within the disintegrin domain (ADAM10$_{D+C}$[RDD-A]), as many disintegrin domains have RGD-like sequences suggested to mediate integrin ligation.

In vitro binding analysis (FIG. 4a) reveals that the ADAM10$_{D+C}$[EEE-A] mutant does not bind the EphA3/ephrin-A5 complex, while ADAM10$_{D+C}$[RDD-A] retains wild-type binding affinity for this ADAM substrate. The mutations did not affect binding to ephrin-A1 and -A2 (data not shown), or affect the overall fold and stability of ADAM10$_{D+C}$ as the mutant proteins were biochemically, apart from their distinct binding affinities for the EphA3/ephrin-A5 complex, undistinguishably from wild-type ADAM10$_{D+C}$. Neither did they affect the Eph-independent binding to ephrin-A1 and -A2 (data not shown).

Importantly, incorporation of the EEE-A amino acid substitutions into cell-surface ADAM10Δpro likewise significantly inhibited its interaction with the EphA3/ephrin-A5 complex, whereas its ephrin-independent constitutive association with EphA3 remained unchanged (FIG. 4b). These results strongly suggest that the negatively-charged pocket within the Cys-rich domain of ADAM10 mediates the recognition and binding to the EphA3/ephrin-A5 complex, while a second EphA3-interaction site outside the ADAM10 Cys-rich domain mediates the weaker constitutive association with unligated EphA3.

To further assess the physiological relevance of this putative substrate recognition site and the functional consequence of its mutation, we introduced the alanine (as well as lysine) substitutions of Glu573, Glu578 and Glu579 into full-length (f.l.) ADAM10. EphA3-expressing 293 cells, transfected with either wild type (wt) or mutant ADAM10[EEE-A], or with catalytically-inactive (dominant-negative) ADAM10$_{AMP}$, were treated with non-clustered or antibody cross-linked ephrin-A5-Fc.

To monitor protease activity, cleaved ephrin-A5 was extracted from the pooled culture medium and cell lysates. Notably, overexpression of mutant ADAM10 with Ala or Lys substitutions of the three Glu residues or lacking the protease domain, effectively inhibited ephrin-A5 cleavage (FIG. 4c), confirming that ADAM10 cleavage of clustered ephrin bound to the surface of EphA3-expressing cells relies on the intact recognition pocket of ADAM10. Interestingly, overexpression of wt-ADAM10 did not increase ephrin cleavage above control levels, in line with the notion that cell-surface EphA3, and thus the amount of ephrin-A5 involved in active signalling complexes, is rate limiting for the cleavage reaction.

To examine the physiological relevance of the substrate-recognition site for ADAM function in intact cells, we performed confocal imaging of HEK293 cells transfected to co-express wild-type or mutant ADAM10 with diHcRed-tagged EphA3, which were co-cultured with cells expressing GFP-tagged ephrin-A5 or GFP-tagged ephrin-A2 (Hattori et al., 2000, supra; Wimmer-Kleikamp et al., 2004, supra) (FIG. 4e). The appearance of punctate ephrin-specific staining within the EphA3-expressing cells is indicative of effective ephrin cleavage and subsequent internalization. To confirm the expression of the HA-tagged, w/t or [EEE-A]-mutant ADAM10, the transfected, diHcRed-EphA3/HEK293 cells were stained with anti-HA and Alexa$^{647}$-labelled secondary antibodies, revealing a purple merged image of cells co-expressing both proteins. Ephrin internalisation is readily noticeable in w/t ADAM10-expressing cells (FIG. 4e, white arrow heads), but is absent in cells expressing the ADAM10 [EEE-A] mutant. In stark contrast, the latter cells are discernible by the appearance of distinct, dense cell surface clusters of uncleaved and non-internalized GFP-ephrin at the points of contact between Eph and ephrin expressing cells (Arrows in FIG. 4e). Taken together, these experiments demonstrate the role of the acidic pocket within the ADAM10 Cys-rich domain to mediate an interaction with the EphA3-ephrinA5/A2 substrate that is essential for ephrin cleavage from the cell surface.

ADAM-mediated ligand cleavage from the cell surface, also referred to as 'shedding' has been extensively described as mechanism that facilitates the release of the pro-forms of the EGF-receptor ligands (Blobel, 2005, supra). We were interested to see, if the here described substrate recognition site of ADAM10 would function also to recognise pro-EGF and regulate its shedding from the cell surface. We performed the same confocal imaging approach, using HEK293 cells transfected to express GFP-tagged EGF-receptor, which were co-cultured with cells expressing HA-tagged pro-EGF. The cells were co-transfected either with wild-type (w/t) ADAM10 or the 3A Adam10 mutant, defect in the substrate recognition groove. The appearance of EGF-specific staining on the EGF-receptor/w/t ADAM10 co-expressing cells is indicative of effective EGF cleavage and subsequent uptake into the EGF-receptor-expressing cells (FIG. 5). Indeed, overexpression of the 3A-ADAM10 mutant dramatically reduced EGF shedding and uptake into adjacent EGF-receptor expressing cells, suggesting that also in this important receptor tyrosine kinase signaling system, recognition of the ligand, in this case pro-EGF by the recognition site in the ADAM10 cysteine-rich domain is critical for subsequent shedding to occur.

Figure 6A:
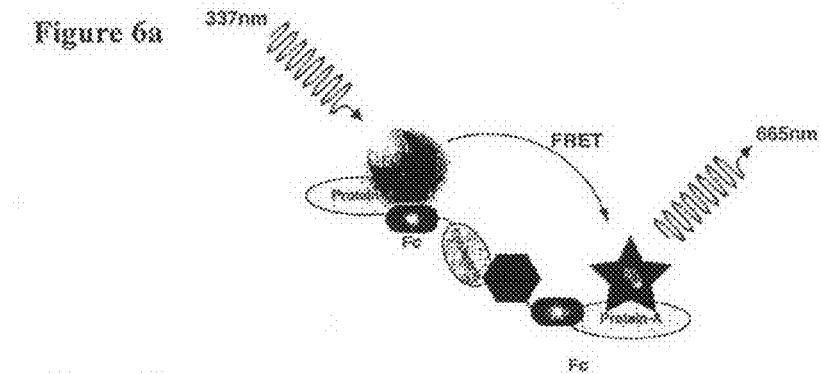
Figure 6B:
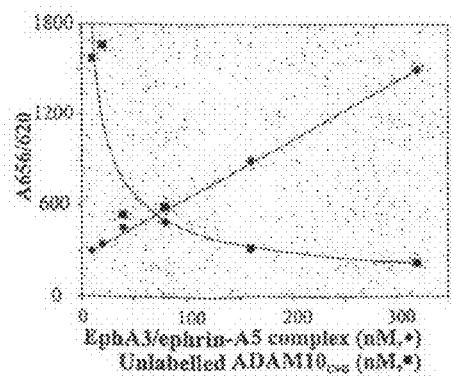

We suggest that our recent elucidation of the ADAM10 disintegrin-cysteine-rich domain structure, exposing a recognition surface for the ephrin-A5/EphA3 complex, now provides a structural basis for integrated, structure-based screening for compounds inhibiting this contact. The proposed drug screening approach is based on homogeneous time resolved fluorescence HTRF™ technology utilising donor and acceptor fluorescence labels that are conjugated to Fc-tagged proteins. The HTRF methodology relies on the energy transfer from an excited fluorescent donor and nearby acceptor molecule. Rare earth metal chelates, such as the $Eu^{3+}$ chelate cryptate (Cis Bio International), with peak excitation at 337 nm, are used as fluorescence donors, while a modified allophycocyanin (XL665) is used as the acceptor with a peak emission at 665 nm. As energy transfer occurs, emission at 665 nm is observed only when the cryptate and XL665 are in close proximity. An interaction between the proteins brings the labels into proximity (within the nanometer range) and triggers fluorescence resonance energy transfer (FRET), which initiates a chemical reaction cascade to produce an amplified fluorescent signal (FIG. 6A). To assess the feasibility of this FRET-based assay, we have used donor-labelled ephrin-A5/EphA3 complex interacting with acceptor-labelled $ADAM10_{D+C}$ (FIG. 6b). As a control for inhibition of binding, we performed a parallel experiment with unlabelled $ADAM10_{D+C}$ demonstrating the capability to monitor competitive inhibition of the association between the labeled target protein ($ADAM10_{D+C}$) and the ephrin/Eph complex.

The elucidation of the structure of the ADAM10 disintegrin and cysteine-rich domains, and the accompanying functional and mutagenesis approaches, have uncovered a substrate-recognition module that is essential for functional association with ephrin/EphA complexes and subsequent positioning of the proteinase domain in a conformation allowing substrate cleavage at a specific site. We have demonstrated the important role of this alignment for the cleavage of ephrin-A2, ephrin-A5 and pro-EGF on a cellular level and our in-vitro binding data suggest that this region of ADAM17 also specifies cleavage of B-type ephrins.

Our observation that the Eph/ephrin complex, rather than the individual proteins, is required for effective binding and proteolytic activity suggests a simple mechanism for regulation of ephrin cleavage. Specifically, based on our data, we propose the following molecular mechanism that ensures that only ephrins bound to Ephs in an active configuration are recognized and cleaved to allow their internalisation into the Eph-expressing cell: First, prior to cell-cell contact ADAM10 is constitutively associated with EphA3. This ensures that upon assembly of the EphA3/ephrin complexes the proteinase is in close proximity to its substrate. We do not exclude the possibility that in some cases ADAM10 might be brought to the Eph/ephrin complex via constitutive interactions with ephrin, such as the one described for ephrin-A2 in.

Our structure-based mutagenesis suggests that the weaker, constitutive EphA3-ADAM10 association is mediated via an additional interface outside the acidic substrate-binding ADAM10 pocket, but still involving the ligand-binding region of EphA3. Second, upon cell-cell contact high-affinity EphA3/ephrin-A5 complexes are formed, presenting a new recognition surface for ADAM10. ADAM10 binds the EphA3/ephrin-A5 complex, most likely at the Eph/ephrin interface, via the substrate-binding pocket of the cys-rich domain. Third, the disintegrin domain, which forms a continuous, rigid structure with the cysteine-rich domain, positions the adjacent N-terminal proteinase domain so that it can efficiently cleave its target—the stem region of ephrin-A5 that connects the ligand-binding domain to the membrane. Fourth, the proteolytic cleavage of ephrin-A5 breaks the molecular tethers between the opposing cell surfaces, allowing for signal termination and for internalisation of the very stable EphA3/ephrin-A5 complexes in the Eph-expressing cell. The constitutive ADAM10-EphA3 interaction suggests that the functional ADAM10 is located on the interacting cell that expresses the Eph receptor, while the cleaved ephrin-A5 is located on the opposite cell. This notion is supported by our demonstration of controlled ephrin cleavage upon addition of ephrin-expressing cells to ADAM- and Eph-expressing cells (FIG. 5d), which can be abrogated by overexpression of ADAM10Δpro on the latter cells. In line with this notion, we find also some constitutive association between Eph and unprocessed endogenous ADAM10 (FIG. 1a), likely to be intracellular (Sundberg et al., 2004, supra). Nevertheless, a detailed molecular understanding of the precise positioning and interactions between Ephs, ephrins and ADAM10 must await further crystallographic studies of the entire triple complex.

The identification of a well-structured surface pocket within the extracellular domain of ADAM10 that mediates ephrin cleavage provides an ideal target for structure-based computational and high-throughput screens for small-molecule substrate-specific ADAM inhibitors. Ephs and ephrins are both upregulated in a range of cancers and potentially promote both tumour growth (through angiogenesis) and invasion (through control of cell adhesion/repulsion). Expression of EphA3, for example, is upregulated in malignant melanomas and ephrin-A5 induces de-adhesion and invasion of EphA3-expressing melanoma cells. Thus targeting the action of ADAM10 on ephrin cleavage could provide an important therapeutic intervention of tumour development, invasion and metastasis.

In addition to ephrins, ADAM10 and ADAM17 are also implicated in cleavage of a range of membrane-bound proteins. These include the ligands for the epidermal growth factor receptor (Sahin et al., 2004, J. Cell Biol. 164 769-779), chemokine ligands CXCL1 (Hundhausen et al., 2003, Blood. 102 1186-1195) and CXCL16 (Abel et al., 2004, J Immunol. 172 6362-6372), as well as the adhesion molecules L1 (Gutwein et al., 2003, FASEB J. 17 292-294) and CD44 (Nagano et al., 2004, J. Cell Biol. 165 893-902) which, like the ephrins, are involved in control of cell migration and/or adhesion. Other ADAM10 functions include shedding of growth factors such as the Notch ligand Delta (Qi et al., 1999, Science 283 91-94), the IL-6R (Matthews et al., 2003, J. Biol. Chem. 278 38829-38839) and Notch (Pan & Rubin, 1997, Cell 90 271-280; Lieber et al., 2002, Genes Dev. 16 209-221). Interestingly, protease cleavage of Notch is dependent on ligand-receptor interaction (Mumm et al., 2000, Molecular Cell. 5

197-206) analogous to the ephrin-Eph system described here, indicative of an evolutionary-conserved mechanism. Furthermore, as discussed above, the regulation and specificity of other ADAM family members is also dependent on the ADAM cysteine-rich domain (Smith et al., 2002, supra; Reddy et al., 2000, supra). Therefore the region we have identified as regulating ADAM10/ADAM17 cleavage of ephrin-ligands might have relevance also for other disease-related targets of ADAM10 and ADAM17.

Throughout this specification, the aim has been to describe the preferred embodiments of the invention without limiting the invention to any one embodiment or specific collection of features. Various changes and modifications may be made to the embodiments described and illustrated herein without departing from the broad spirit and scope of the invention.

All computer programs, algorithms, patent and scientific literature referred to herein is incorporated herein by reference in their entirety.

The invention claimed is:

1. An isolated monoclonal antibody or a fragment thereof raised against a substrate recognition site within a cysteine-rich domain of human A Disintegrin And Metalloprotease 10 (ADAM10) protease, wherein the substrate recognition site comprises amino acid residues 573-579 of said ADAM10 protease and wherein said isolated monoclonal antibody or fragment thereof binds one or more of said amino acid residues 573-579 of said ADAM10 protease.

2. An isolated monoclonal antibody or a fragment thereof that binds one or more of amino acid residues 573-579 of human A Disintegrin And Metalloprotease 10 (ADAM10) protease.

3. The isolated monoclonal antibody or fragment thereof of claim 2, wherein binding of said one or more of amino acid residues 573-579 of human ADAM10 protease inhibits the binding of said ADAM10 protease to one or more of its substrates.

* * * * *

SEQUENCE LISTING

```
<160> NUMBER OF SEQ ID NOS: 20

<210> SEQ ID NO 1
<211> LENGTH: 7
<212> TYPE: PRT
<213> ORGANISM: Homo sapiens

<400> SEQUENCE: 1

Glu Lys Tyr Gly Leu Glu Glu
1               5

<210> SEQ ID NO 2
<211> LENGTH: 8
<212> TYPE: PRT
<213> ORGANISM: Homo sapiens

<400> SEQUENCE: 2

Glu Arg Glu Gln Gln Leu Glu Ser
1               5

<210> SEQ ID NO 3
<211> LENGTH: 21
<212> TYPE: DNA
<213> ORGANISM: Bos taurus

<400> SEQUENCE: 3
gagaaacatg gcttggagga g                                              21

<210> SEQ ID NO 4
<211> LENGTH: 21
<212> TYPE: DNA
<213> ORGANISM: Bos taurus

<400> SEQUENCE: 4
gcgaaacatg gcttggcggc g                                              21

<210> SEQ ID NO 5
<211> LENGTH: 21
<212> TYPE: DNA
<213> ORGANISM: Mus musculus

<400> SEQUENCE: 5
gaaaagtatg acttggagga g                                              21

<210> SEQ ID NO 6
<211> LENGTH: 21
<212> TYPE: DNA
<213> ORGANISM: Mus musculus

<400> SEQUENCE: 6
gcaaagtatg acttggcggc g                                              21

<210> SEQ ID NO 7
```

-continued

```
<211> LENGTH: 21
<212> TYPE: DNA
<213> ORGANISM: Homo sapiens

<400> SEQUENCE: 7
gagaaatatg gcttagagga g                                              21

<210> SEQ ID NO 8
<211> LENGTH: 21
<212> TYPE: DNA
<213> ORGANISM: Homo sapiens

<400> SEQUENCE: 8
gcgaaatatg gcttagcggc g                                              21

<210> SEQ ID NO 9
<211> LENGTH: 24
<212> TYPE: DNA
<213> ORGANISM: Homo sapiens

<400> SEQUENCE: 9
gagagggaac agcagctgga gtcc                                           24

<210> SEQ ID NO 10
<211> LENGTH: 24
<212> TYPE: DNA
<213> ORGANISM: Homo sapiens

<400> SEQUENCE: 10
gcgagggaac agcagctggc ggcc                                           24

<210> SEQ ID NO 11
<211> LENGTH: 21
<212> TYPE: DNA
<213> ORGANISM: Artificial sequence
<220> FEATURE:
<223> OTHER INFORMATION: ADAM10 siRNA construct

<400> SEQUENCE: 11
ugggcaaugu gcagguucut t                                              21

<210> SEQ ID NO 12
<211> LENGTH: 23
<212> TYPE: DNA
<213> ORGANISM: Artificial sequence
<220> FEATURE:
<223> OTHER INFORMATION: ADAM10 siRNA construct

<400> SEQUENCE: 12
aaugaagagg gacacuuccc utt                                            23

<210> SEQ ID NO 13
<211> LENGTH: 23
<212> TYPE: DNA
<213> ORGANISM: Artificial sequence
<220> FEATURE:
<223> OTHER INFORMATION: ADAM10 siRNA construct

<400> SEQUENCE: 13
aaguugccuc cuccuaaacc att                                            23

<210> SEQ ID NO 14
<211> LENGTH: 191
<212> TYPE: PRT
<213> ORGANISM: Bos taurus
```

```
<400> SEQUENCE: 14

Ser Gly Gln Pro Ile Cys Gly Asn Gly Met Val Glu Gln Gly Glu Glu
1               5                   10                  15

Cys Asp Cys Gly Tyr Ser Asp Gln Cys Lys Asp Glu Cys Cys Tyr Asp
                20                  25                  30

Ala Asn Gln Pro Glu Gly Lys Lys Cys Lys Leu Lys Pro Gly Lys Gln
            35                  40                  45

Cys Ser Pro Ser Gln Gly Pro Cys Cys Thr Ala His Cys Ala Phe Lys
50                  55                  60

Ser Lys Thr Glu Lys Cys Arg Asp Asp Ser Asp Cys Ala Lys Glu Gly
65                  70                  75                  80

Ile Cys Asn Gly Ile Thr Ala Leu Cys Pro Ala Ser Asp Pro Lys Pro
                85                  90                  95

Asn Phe Thr Asp Cys Asn Arg His Thr Gln Val Cys Ile Asn Gly Gln
            100                 105                 110

Cys Ala Gly Ser Ile Cys Glu Lys His Gly Leu Glu Glu Cys Thr Cys
        115                 120                 125

Ala Ser Ser Asp Gly Lys Asp Asp Lys Glu Leu Cys His Val Cys Cys
130                 135                 140

Met Lys Lys Met Glu Pro Ser Thr Cys Ala Ser Thr Gly Ser Val Gln
145                 150                 155                 160

Trp Asn Lys Tyr Phe Leu Gly Arg Thr Ile Thr Leu Gln Pro Gly Ser
                165                 170                 175

Pro Cys Asn Asp Phe Arg Gly Tyr Cys Asp Val Phe Met Arg Cys
            180                 185                 190

<210> SEQ ID NO 15
<211> LENGTH: 190
<212> TYPE: PRT
<213> ORGANISM: Homo sapiens

<400> SEQUENCE: 15

Lys Gln Gln Ala Val Cys Gly Asn Ala Lys Leu Glu Ala Gly Glu Glu
1               5                   10                  15

Cys Asp Cys Gly Thr Glu Gln Asp Cys Ala Leu Ile Gly Glu Thr Cys
                20                  25                  30

Cys Asp Ile Ala Thr Cys Arg Phe Lys Ala Gly Ser Asn Cys Ala Glu
            35                  40                  45

Gly Pro Cys Cys Glu Asn Cys Leu Phe Met Ser Lys Glu Arg Met Cys
50                  55                  60

Arg Pro Ser Phe Glu Glu Cys Asp Leu Pro Glu Tyr Cys Asn Gly Ser
65                  70                  75                  80

Ser Ala Ser Cys Pro Glu Asn His Tyr Val Gln Thr Gly His Pro Cys
                85                  90                  95

Gly Leu Asn Gln Trp Ile Cys Ile Asp Gly Val Cys Met Ser Gly Asp
            100                 105                 110

Lys Gln Cys Thr Asp Thr Phe Gly Lys Glu Val Glu Phe Gly Pro Ser
        115                 120                 125

Glu Cys Tyr Ser His Leu Asn Ser Lys Thr Asp Val Ser Gly Asn Cys
130                 135                 140

Gly Ile Ser Asp Ser Gly Tyr Thr Gln Cys Glu Ala Asp Gly His Leu
145                 150                 155                 160

Cys Ile Ala Val Glu Phe Ala Ser Asp His Ala Asp Ser Gln Lys Met
                165                 170                 175

Trp Ile Lys Asp Gly Thr Ser Cys Gly Ser Asn Lys Val Cys
```

```
                180                 185                 190

<210> SEQ ID NO 16
<211> LENGTH: 222
<212> TYPE: PRT
<213> ORGANISM: Xenopus laevis

<400> SEQUENCE: 16

Val Met Gly Lys Lys Cys Gly Asn Gly Phe Leu Glu Glu Gly Glu Gln
1               5                   10                  15

Cys Asp Cys Gly Glu Pro Glu Glu Cys Thr Asn Ser Cys Cys Asn Ala
            20                  25                  30

Asn Asn Cys Thr Leu Lys Ala Gly Ala Gln Cys Ala His Gly Glu Cys
        35                  40                  45

Cys Gln Asp Cys Lys Leu Lys Ser Ala Gly Thr Gln Cys Arg Glu Met
    50                  55                  60

Ala Gly Ser Cys Asp Leu Pro Glu Phe Cys Thr Gly Asp Ala Pro Ser
65                  70                  75                  80

Cys Pro Ser Asn Val Tyr Lys Leu Asp Gly Ser Leu Cys Ala Asp Gly
                85                  90                  95

Asn Ala Tyr Cys Tyr Asn Gly Met Cys Leu Thr His Gln Gln Gln Cys
            100                 105                 110

Ile His Leu Trp Gly Ser Gly Ala Val Val Ala Pro Asn Phe Cys Phe
        115                 120                 125

Gln Asp Val Asn Lys Ala Gly Asp Gln Tyr Gly Asn Cys Gly Lys Asn
    130                 135                 140

Gly Arg Gly Gln Phe Val Lys Cys Thr Ser Arg Asp Ala Lys Cys Gly
145                 150                 155                 160

Lys Ile Gln Cys Gln Thr Ser Ser Glu Lys Pro Arg Asp Pro Ser Met
                165                 170                 175

Val Lys Val Asp Asn Thr Ile Ile Ile Asn Gly Tyr Lys Met Lys Cys
            180                 185                 190

Gln Gly Val His Ala Tyr Ser Met Gln Glu Glu Gly Asp Pro Gly
        195                 200                 205

Leu Val Met Thr Gly Thr Lys Cys Gly Asp Gly Met Val Cys
    210                 215                 220

<210> SEQ ID NO 17
<211> LENGTH: 223
<212> TYPE: PRT
<213> ORGANISM: Rattus norvegicus

<400> SEQUENCE: 17

Pro Met Ser Ser Leu Cys Gly Asn Met Phe Val Asp Pro Gly Glu Gln
1               5                   10                  15

Cys Asp Cys Gly Phe Pro Asp Glu Cys Thr Asp Pro Cys Cys Asp Tyr
            20                  25                  30

Phe Thr Cys Gln Leu Arg Pro Gly Ala Gln Cys Ala Ser Asp Gly Pro
        35                  40                  45

Cys Cys Gln Asn Cys Lys Leu Gln Pro Ala Gly Trp Gln Cys Arg Leu
    50                  55                  60

Pro Thr Asp Asp Cys Asp Leu Pro Glu Phe Cys Leu Gly Asp Ser Ser
65                  70                  75                  80

Gln Cys Pro Pro Asp Ile Arg Leu Gly Asp Gly Glu Pro Cys Ala Ser
                85                  90                  95

Gly Glu Ala Val Cys Met His Gly Arg Cys Ala Ser Tyr Thr Arg Gln
            100                 105                 110
```

```
Cys Gln Ser Leu Trp Gly Pro Gly Ala Gln Pro Ala Ala Pro Leu Cys
            115                 120                 125

Leu Gln Thr Ala Asn Thr Arg Gly Asn Ala Phe Gly Ser Cys Gly Arg
    130                 135                 140

Ser Pro Ser Gly Ser Tyr Met Pro Cys Asn Leu Arg Asp Ala Ile Cys
145                 150                 155                 160

Gly Gln Leu Gln Cys Gln Trp Gly Arg Asn Gln Pro Leu Leu Gly Ser
                165                 170                 175

Val Gln Asp Gln Leu Ser Glu Val Leu Glu Ala Asn Gly Thr Gln Leu
            180                 185                 190

Asn Cys Ser Trp Val Asp Leu Asp Leu Gly Asn Asp Val Ala Gln Pro
        195                 200                 205

Leu Leu Ala Leu Pro Gly Thr Ala Cys Gly Pro Gly Leu Val Cys
    210                 215                 220

<210> SEQ ID NO 18
<211> LENGTH: 175
<212> TYPE: PRT
<213> ORGANISM: Mus musculus

<400> SEQUENCE: 18

Arg Ser Asn Lys Val Cys Gly Asn Ser Arg Val Asp Glu Gly Glu Glu
1               5                   10                  15

Cys Asp Pro Gly Ile Met Tyr Leu Asn Asn Asp Thr Cys Cys Asn Ser
            20                  25                  30

Asp Cys Thr Leu Lys Pro Gly Val Gln Cys Ser Asp Arg Asn Ser Pro
        35                  40                  45

Cys Cys Lys Asn Cys Gln Phe Glu Thr Ala Gln Lys Lys Cys Gln Glu
    50                  55                  60

Ala Ile Asn Ala Thr Cys Lys Gly Val Ser Tyr Cys Thr Gly Asn Ser
65                  70                  75                  80

Ser Glu Cys Pro Pro Pro Gly Asp Ala Glu Asp Asp Thr Val Cys Leu
                85                  90                  95

Asp Leu Gly Lys Cys Lys Ala Gly Lys Cys Ile Pro Phe Cys Lys Arg
            100                 105                 110

Glu Gln Glu Leu Glu Ser Cys Ala Cys Val Asp Thr Asp Asn Ser Cys
        115                 120                 125

Lys Val Cys Cys Arg Asn Leu Ser Gly Pro Cys Val Pro Tyr Val Asp
    130                 135                 140

Ala Glu Gln Lys Asn Leu Phe Leu Arg Lys Gly Lys Pro Cys Thr Val
145                 150                 155                 160

Gly Phe Cys Asp Met Asn Gly Lys Cys Glu Lys Arg Val Gln Asp
                165                 170                 175

<210> SEQ ID NO 19
<211> LENGTH: 222
<212> TYPE: PRT
<213> ORGANISM: Homo sapiens

<400> SEQUENCE: 19

Gln Asn Gln Pro Val Cys Gly Asn Gly Ile Leu Glu Ser Asn Glu Glu
1               5                   10                  15

Cys Asp Cys Gly Asn Lys Asn Glu Cys Gln Phe Lys Lys Cys Cys Asp
            20                  25                  30

Tyr Asn Thr Cys Lys Leu Lys Gly Ser Val Lys Cys Gly Ser Gly Pro
        35                  40                  45
```

-continued

```
Cys Cys Thr Ser Lys Cys Glu Leu Ser Ile Ala Gly Thr Pro Cys Arg
 50                  55                  60
Lys Ser Ile Asp Pro Glu Cys Asp Phe Thr Glu Tyr Cys Asn Gly Thr
 65                  70                  75                  80
Ser Ser Asn Cys Val Pro Asp Thr Tyr Ala Leu Asn Gly Arg Leu Cys
                 85                  90                  95
Lys Leu Gly Thr Ala Tyr Cys Tyr Asn Gly Gln Cys Gln Thr Thr Asp
            100                 105                 110
Asn Gln Cys Ala Lys Ile Phe Gly Lys Gly Ala Gln Gly Ala Pro Phe
        115                 120                 125
Ala Cys Phe Lys Glu Val Asn Ser Leu His Glu Arg Ser Glu Asn Cys
    130                 135                 140
Gly Phe Lys Asn Ser Gln Pro Leu Pro Cys Glu Arg Lys Asp Val Leu
145                 150                 155                 160
Cys Gly Lys Leu Ala Cys Val Gln Pro His Lys Asn Ala Asn Lys Ser
                165                 170                 175
Asp Ala Gln Ser Thr Val Tyr Ser Tyr Ile Gln Asp His Val Cys Val
            180                 185                 190
Ser Ile Ala Thr Gly Ser Ser Met Arg Ser Asp Gly Thr Asp Asn Ala
        195                 200                 205
Tyr Val Ala Asp Gly Thr Met Cys Gly Pro Glu Met Tyr Cys
    210                 215                 220

<210> SEQ ID NO 20
<211> LENGTH: 208
<212> TYPE: PRT
<213> ORGANISM: Rattus norvegicus

<400> SEQUENCE: 20

Ile Ser Thr Pro Val Cys Gly Asn Gln Leu Leu Glu Met Asn Glu Asp
  1               5                  10                  15
Cys Asp Cys Gly Thr Pro Lys Glu Cys Thr Asn Lys Cys Cys Asp Ala
                 20                  25                  30
Glu Thr Cys Lys Ile Lys Ala Gly Phe Gln Cys Ala Leu Gly Glu Cys
            35                  40                  45
Cys Glu Lys Cys Gln Leu Lys Lys Pro Gly Val Val Cys Arg Ala Ala
    50                  55                  60
Lys Asp Glu Cys Asp Leu Pro Glu Met Cys Asp Gly Lys Ser Ser His
 65                  70                  75                  80
Cys Pro Val Asp Arg Phe Arg Val Asn Gly Phe Pro Cys Gln Asn Gly
                 85                  90                  95
His Gly Tyr Cys Leu Lys Gly Asn Cys Pro Thr Leu Gln Gln Gln Cys
            100                 105                 110
Met Asp Met Trp Gly Pro Glu Thr Lys Val Ala Asn Lys Ser Cys Tyr
        115                 120                 125
Lys Gln Asn Glu Gly Gly Ser Lys Tyr Gly Tyr Cys His Val Glu Asn
    130                 135                 140
Gly Thr His Met Pro Cys Lys Ala Lys Asp Ala Met Cys Gly Lys Leu
145                 150                 155                 160
Phe Cys Glu Gly Gly Ser Gly Asp Leu Pro Trp Lys Gly Leu Thr Ile
                165                 170                 175
Ala Phe Leu Thr Cys Lys Leu Phe Asp Pro Glu Asp Ile Asn Gln Gly
            180                 185                 190
Val Asp Met Val Ala Asn Gly Thr Lys Cys Gly Asn Asn Lys Val Cys
        195                 200                 205
```